United States Patent [19]

Johnson

[11] Patent Number: 4,701,174
[45] Date of Patent: Oct. 20, 1987

[54] FORM-FITTING SELF-ADJUSTING DISPOSABLE GARMENT WITH ANGLED DIRECTION STRETCHABLE OUTER COVER

[75] Inventor: Lynn A. Johnson, DePere, Wis.

[73] Assignee: Kimberly-Clark Corporation, Neenah, Wis.

[21] Appl. No.: 773,745

[22] Filed: Sep. 6, 1985

[51] Int. Cl.[4] .................................. A61F 13/16
[52] U.S. Cl. .................. 604/385 A; 604/387; 604/355 R; 604/317
[58] Field of Search .............. 604/370, 385.2, 385.1, 604/396–399, 389–390

[56] References Cited

U.S. PATENT DOCUMENTS

| 1,678,166 | 7/1928 | Repay | 24/575 |
| 4,022,210 | 5/1977 | Glassman | 604/389 |
| 4,041,949 | 8/1977 | Kozak | 604/370 |
| 4,166,464 | 9/1979 | Korpman | 604/370 |
| 4,229,835 | 10/1980 | Shaw | 604/385.2 |
| 4,425,128 | 1/1984 | Motomura | 604/385.2 |

Primary Examiner—C. Fred Rosenbaum
Assistant Examiner—Denise Whelton
Attorney, Agent, or Firm—John L. Chiatalas

[57] ABSTRACT

An anatomically form-fitting, self-adjusting disposable garment with a stretchable outer cover (20), stretchable at an angle (23) from the cross body direction (25). An absorbent structure (22) is disposed within the outer cover (20) in such a way that the stretchability of the outer cover (20) is uninhibited. Fixed position fasteners (70) (72) (74) (76) are attached to the outer cover (20).

17 Claims, 31 Drawing Figures

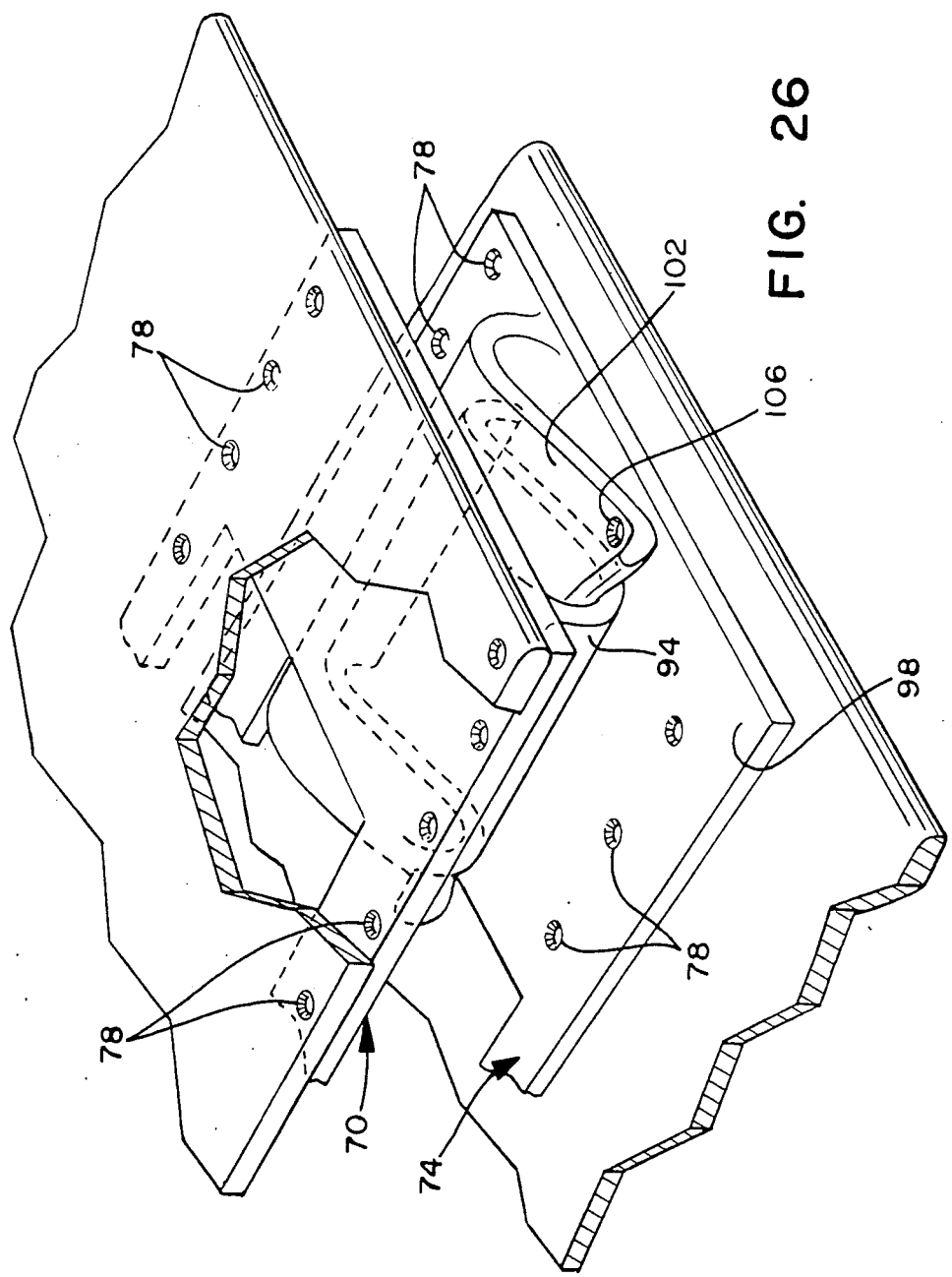

4,701,174

FORM-FITTING SELF-ADJUSTING DISPOSABLE GARMENT WITH ANGLED DIRECTION STRETCHABLE OUTER COVER

TECHNICAL FIELD

The present invention relates, generally, to the field of disposable garments utilized for the absorption and containment of urine and other body exudates. More particularly, the present invention relates to form-fitting, self-adjusting disposable garments with fixed position fasteners. Most particularly, the present invention relates to disposable diapers that provide enhanced fit and functionality through novel construction utilizing novel materials.

BACKGROUND ART

Disposable garments are generally well known in the art and have become an important and an essentially indispensable sanitary protection item, most particularly in the field of infant and child care where disposable diapers provide for the absorption and containment of urine and other body exudates. Present commercially available disposable diapers are generally unitary, preshaped and prefolded, and comprised in a porous facing layer, a fluid impervious backing sheet with an absorbent material disposed therebetween. These presently available disposable diapers have met a particular need and have become ever increasingly popular. However, even though the presently available disposable diapers are efficient and effective they have several drawbacks that have been identified by mothers of infants wearing the diapers. These mothers have strongly voiced their desire to be able to obtain disposable diapers that are aesthetically neat and attractive when on their infant or child. The aesthetically neat criteria have been identified as including a trim, slim fit, and a neat fitting waist and legs that do not allow leakage of urine or feces. It has also been found that mothers do not want their children to look rumpled, bulky, or messy. In addition, these mothers have expressed a desire to either have a disposable diaper that fits more sizes of babies or to have disposable diapers provided in more sizes.

Another drawback identified by these mothers has been the problem associated with skin irritation caused by urine, feces, or moisture trapped next to the skin. They have again been very vocal in their desire to obtain disposable diapers that avoid or solve this problem.

Another major drawback is associated with the methods provided to secure the diaper around the baby. The method most utilized in present commercially available disposable diapers is the plastic sealable tape. Initially, the fastening tapes introduced on disposable diapers were not resealable, which meant that when the mother wished to check the diaper for wetness or to adjust the fit, the tapes could not be resealed. This, in turn, meant that the diaper, if not ready to be changed, would have to be thrown away. Presently, disposable diapers use tapes that are manufactured to be resealable. However, it has been found that the tapes presently used are subject to contamination by baby powder or baby oil or other substances which prevent them from resealing, or in the worst case, prevent them from sealing up initial use. The mothers indicate that they want disposable diapers that have fasteners that are not subject to contamination, that are always resealable and that are not easily unfastenable by babies. The attempt to provide tapes that are always resealable has caused some manufacturers to utilize stronger adhesives on the tapes. Unfortunately, however, the stronger adhesives have a tendency to tear the outer cover which may also cause the diaper to be unusable.

Furthermore, the fastening tapes used on the present disposable diaper can also have a detrimental effect upon fit. Because the tapes are made to be sealable on any portion of the outer cover, and there is no indication to mothers where the tapes should be sealed, the tapes are very often sealed to the outer cover at the wrong position which has several detrimental effects. First, the diaper does not fit on the baby properly, for example, if too loose, the diaper falls down or droops at the waist, or if too tight, causes strain in the outer cover which can make the baby uncomfortable. Second, the improper positioning of the tapes can cause the leg openings to gap thus causing leakage. Third, in an attempt to reposition the tapes to correct the above problems mothers have found that there is an increased potential to contaminate the tapes thus causing the disposable diaper to be unusable.

The attempts to solve the drawbacks associated with present disposable diapers have extended over several years and include several different methods. One method to improve fit involves geometrical folding of rectangular diapers for the purpose of narrowing the apparent width in the crotch area. One method is taught in U.S. Pat. No. Re. 26,151 to Duncan et al. in which a rectangular diaper is provided with parallel longitudinal folded box pleats and a loose overlying flap along each side. Another method is taught in U.S. Pat. No. 3,196,874 to Hrubecky, in which a rectangular diaper is provided with triangular-shaped infolds in the crotch area. These two methods permit the diaper to be more easily fitted to the child, however, problem areas remain. First, the prefolded rectangular diaper results in increased bulk between the legs causing discomfort to the infant. Second, the nonconforming bulk prevents the diaper from closely conforming to the legs leaving gaps which permit leaks to occur. Third, the nonconforming sides tend to pull the waist down at the sides thereby causing the diaper to gap at the front of the waist where leaks can also occur. In addition, the gapping at the front waist contributes to making the diaper appear bulky, sloppy and messy.

To solve the resulting problems associated with the nonconforming bulk between the legs, methods, including reducing the width of the absorbent pad in the crotch area, were tried. However, because the materials used in constructing disposable diapers are relatively nonconformable, a close fit around the thighs is difficult to achieve and undesirable gaps still have a tendency to occur. In addition, the reduced width of the absorbent pad reduces the available absorbent capacity which also further increases the potential for leakage. In an attempt to reduce leakage, U.S. Pat. No. 3,860,003 to Buell provides the diaper edges with elasticized, flexible flaps between the elasticiezed line and the edge of the absorbent pad in the crotch.

Again, an attempt to solve one problem results in the emergence of another problem. Elasticized flaps provide a tight seal at the thighs because the tensioned elastic presses the easily deformable flaps into close contact with the legs. However, the tight seal at the thighs can have several causal effects. First, the tight seal can cause urine to collect near the diaper edges which can permeate into the area between the flap and the skin where it can cause skin irritation. Second, because it is necessary to reduce the absorbent pad width in order to provide the required flap width, the remaining absorbent becomes excessively wet and leaks can still occur. Third, when the reduced width of the absorbent becomes excessively wet, it tends to separate and bunch up at the bottom of the crotch thus hindering fluid transfer to unused portions of the absorbent pad.

To solve the problems associated with elasticized flaps a new and improved disposable diaper is taught in U.S. Pat. No. 4,050,462 to Woon et al. in which the diaper is elasticized only along the edges in a narrowed crotch area in a manner to give a more conformable leg fit as well as improved functional absorbent capacity. This is achieved by attaching the elastic immediately adjacent to the edges of the absorbent pad and also bonding the absorbent pad surface to the backing or facing material in that area to unitize the structure. This causes the absorbent pad to contract when the elastic contracts thus producing gross transverse rugosities in the crotch area. These gross transverse rugosities, inter alia, increase the effective absorbent capacity of the absorbent pad by decreasing the tendency of the absorbent to separate and increasing the wicking characteristics of the absorbent.

The present application teaches an improved disposable diaper which is anatomically form-fitting and anatomically self-adjusting to provide an attractively slim, trim diaper for the baby to wear. The diaper provided by the present invention is trim, does not gap at the legs or waist, and has virtually contamination-proof refastenable fixed position fasteners. Furthermore, the disposable diaper as provided by the present invention is breathable and at the same time highly resistant to leakage.

DISCLOSURE OF THE INVENTION

It has now been determined in accordance with the present invention that an anatomically form-fitting generally self-adjusting disposable diaper can be produced. Advantageously, the disposable diaper of the present invention achieves a considerably improved fit and an attractive appearance when worn by a baby. Furthermore, the components of the disposable diaper of the present invention are constructed in a novel way from novel materials such that the disposable diaper is snug and comfortable and does not irritate the skin of the baby. The outer cover of the disposable diaper of the present invention is not only breathable, but is resiliently stretchable, thus providing both the benefits of dry skin and a form-fitting, anatomically self-adjusting disposable diaper that conforms to the baby's shape. The stretchable outer cover utilized in the disposable diaper of the present invention covers and protects the body in all desired places, provides a gentle, but secure, closure at the waist and legs and resists deformation and degradation during use. Further advantageously, fixed position fasteners provide a solution to many of the problems encountered with the resealable tapes as used in the prior art. The fasteners, in one aspect of the present invention, have multiple refastenability capabilities, are virtually insensitive to contamination, can provide closure from the waist opening to each leg opening, can maintain the distance between the waist opening and each leg opening during use which prevents the waist from sagging and the leg openings from gapping, are flexible so that they do not restrict the baby's motion and since they are fixed position point-to-point fasteners, in a most preferred embodiment, they are virtually impossible to fasten incorrectly. Another advantageous aspect of the present invention is that the waist and leg openings have finished edges, such as hems. The hems provide one aspect of the neat, trim appearance of the present invention.

The foregoing, and other advantages of the present invention, are realized in an anatomically form-fitting, generally self-adjusting disposable diaper comprising an outer cover, an absorbent structure disposed within the outer cover, and fixed position, point-to-point fasteners to secure the diaper around the body of the wearer. The outer cover is resiliently stretchable in at least one direction, in one aspect of the present invention the outer cover is resiliently stretchable in a cross body direction. The outer cover is resiliently stretchable in a range from about 20% to 200%. The self-adjusting feature of the present invention is accomplished by novel construction and novel materials which provide the diaper with a trim, snug appearance when worn by a baby. The resiliently stretchable outer cover allows the diaper to self-adjust to the various shapes and forms of various babies caused by different anatomical features such as varying stomach and thigh sizes. The self-adjusting feature refers to the ability of the diaper to self-adjust to not only the differing anatomical features but to various positions and activities of the baby, for example, the various sleep positions that babies will take, the various play positions as well as the various methods of travel, i.e., walking, crawling or "scooting" along the floor. Whatever the baby is doing, the disposable diaper of the present invention "self-adjusts" to present a slim, trim aesthetically neat appearance.

The advantage of providing the outer cover with stretchability at an angle to the cross body direction is that the angled stretchability provides components of stretchability in both the cross body direction and the vertical direction (defined as parallel to the height direction of a wearer). This provides the functionality of a two-way stretch material using a one-way stretch material.

BRIEF DESCRIPTION OF THE DRAWINGS

FIG. 26 is a perspective view of the two members of the fixed position fastener shown in an interlocked position.

MODES FOR CARRYING OUT THE INVENTION

The present invention relates, generally, to disposable diapers for the absorption and containment of urine and other body exudates. The present invention relates more especially to disposable diapers that are anatomically form-fitting, generally self-adjusting to achieve an aesthetically pleasing fit on the body of a wearer. Most particularly, the present invention provides fixed position fasteners attached to an outer cover for securing the disposable diaper around a wearer. Accordingly, the present invention will now be described with reference to certain modes for carrying out the invention within the aforementioned context. Those skilled in the art will realize that such a description is meant to be exemplary only and should not be deemed limitative respecting the scope of the present invention, for example, in terms of its construction.

Figure 1A:
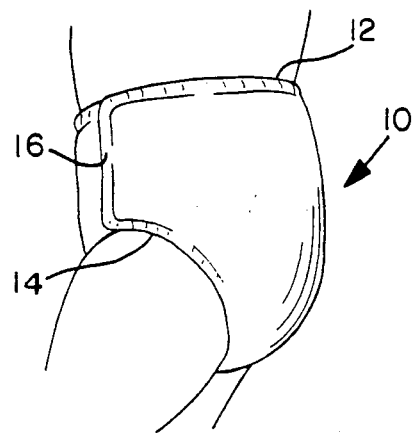
FIG. 1A is a side view of the disposable diaper of the present invention shown secured around a baby.
Figure 1B:
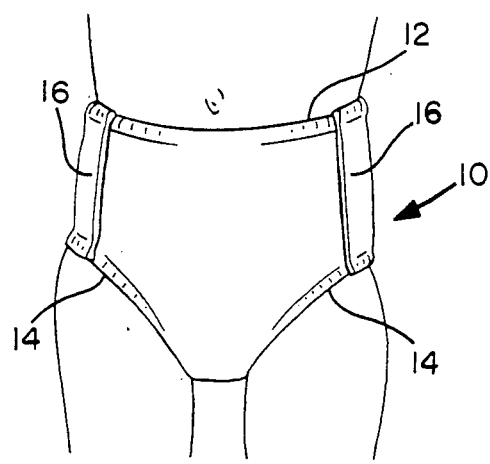
FIG. 1B is a front view of the disposable diaper of the present invention shown secured around a baby.
Figure 1C:
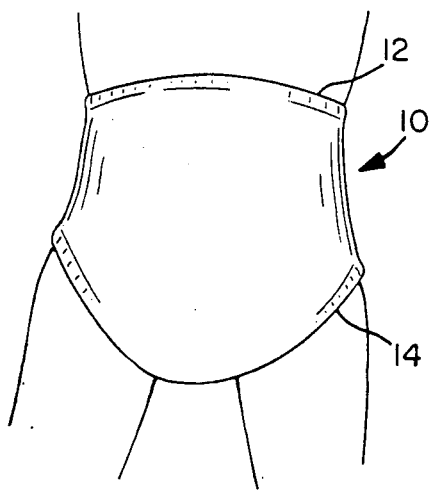
FIG. 1C is a back view of the disposable diaper of the present invention shown secured around a baby.
Figure 1D:
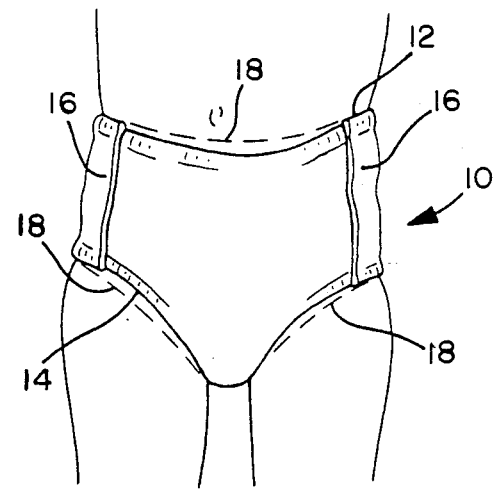
FIG. 1D is a front view of the disposable diaper of the present invention showing the disposition of the diaper on the baby after being worn for a period of time.

Turning to the figures, in each of which like parts are identified with like reference characters, FIGS. 1A through 1D show the disposable diaper 10 as it would be worn by a baby. Indicated at 12 and 14 the waist and leg openings are hemmed. FIGS. 1A, 1B, and 1D indicate generally at 16 the position of the fasteners. FIG. 1D illustrates the minimal extent the diaper moves from an initial position as indicated by the dashed lines 18 after being worn by an infant for a period of time.

Figure 2:
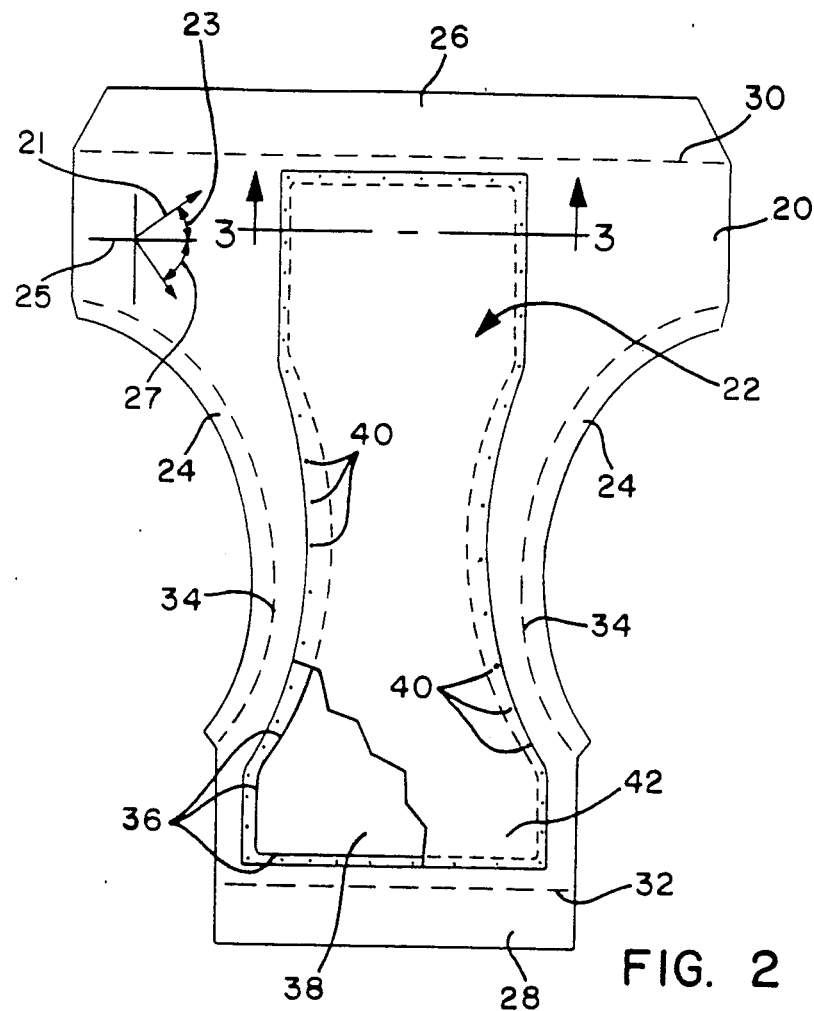
FIG. 2 is a plan view of an embodiment of the disposable diaper of the present invention shown in a semi-finished condition.
Figure 3:
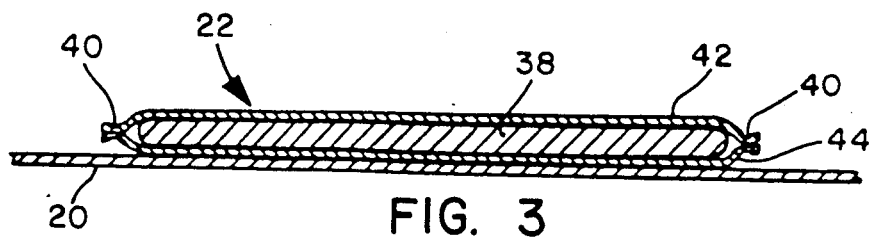
FIG. 3 is a sectional view of cross section 3—3 shown in FIG. 2.

Turning now to FIG. 2, there is shown an embodiment of the disposable diaper provided by the present invention. An outer cover 20 is shown in plan view with an absorbent structure 22 disposed thereon. Outer cover 20 is made from a resiliently stretchable material to be described later. The outer cover 20 is resiliently stretchable in at least one direction indicated at 21 with the stretch direction measured as an angle, indicated at 23, from the cross body direction, indicated at 25. The stretch direction can be at any angle from the cross body direction, however, it is contemplated that the angle should be in the range of ±30° to ±60° with the preferred angle being ±50° (the minus direction is indicated at 27). If the outer cover is made from a material stretchable in only one direction this aspect of the present invention provides components of stretch in both the cross body direction (the horizontal) and the vertical direction. In effect, this provides the functionality of a two-way stretch material with a one-way stretch material. Outer cover 20 is shown with leg hems 24, back waist flap 26 and front waist flap 28 unfolded. Foldline 30 indicates where back waist flap 26 is folded. Similarly, foldline 32 indicates where front waist flap 28 is folded. Foldlines 34 indicate where hems 24 are folded. Line 36 shows the periphery of absorbent composite 38. Referring to FIG. 3 in conjunction with FIG. 2, absorbent structure 22 comprises a liquid permeable bodyside liner 42 bonded to a liquid impermeable barrier 44 with absorbent composite 38 disposed therebetween. It is contemplated that any appropriate means for bonding bodyside liner 42 to barrier 44 may be used. A preferable method of bonding bodyside liner 42 to barrier 44 is any autogenous bonds such as the bonds produced by sonic or ultrasonic energy. A function of the bonding between bodyside liner 42 and barrier 44 is to maintain absorbent composite 38 disposed therebetween and to maintain absorbent structure 22 as a unitary structure. Depending upon the composition of absorbent composite 38 the bonding between bodyside liner 42 and barrier 44 may be continuous or a series of discrete points. It is noted that for the sake of clarity only a few autogenous bonding points 40 are shown and numbered. Other methods, such as pressure or heat sensitive adhesives may be used and are to be considered within the scope of the present invention. As shown in FIG. 3, absorbent structure 22 is disposed upon outer cover 20. The materials making up each component will be discussed in conjunction with later figures.

Figure 4:
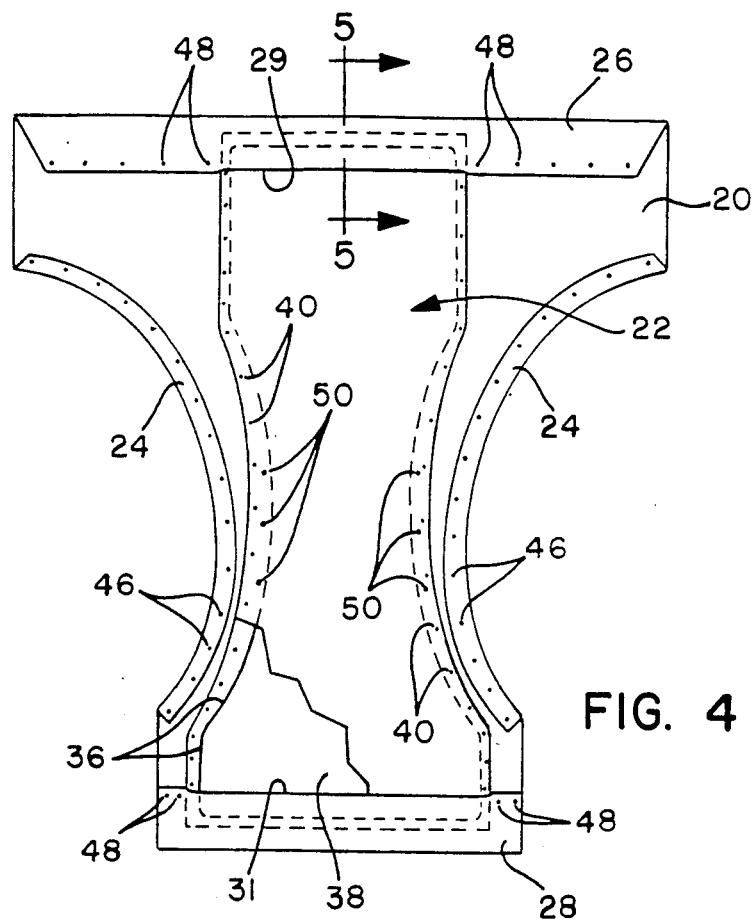
FIG. 4 is a plan view of the disposable diaper shown in FIG. 2 in a finished condition but without fasteners.
Figure 5:
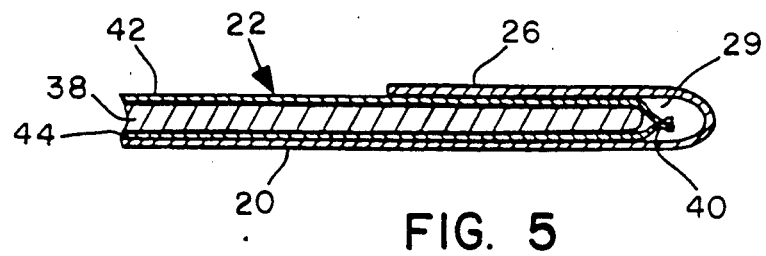
FIG. 5 is a sectional view of cross section 5—5 of FIG. 4.
Figure 6:
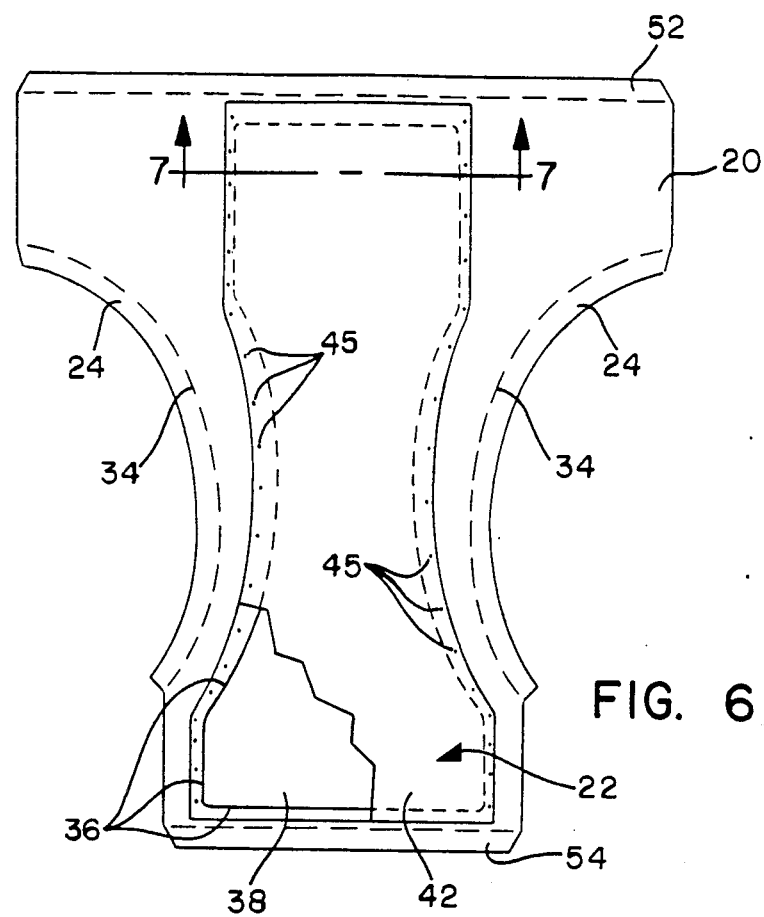
FIG. 6 is a plan view of an alternative embodiment of the disposable diaper of the present invention shown in a semi-finished condition.

Illustrated in FIG. 4 is the embodiment of the disposable diaper shown in FIG. 2 with waist flaps 26 and 28 folded over absorbent structure 22 forming pockets 29 and 31. FIG. 4 also shows hems 24 folded and bonded. Again, any method of bonding may be used, however, autogenous bonding is a preferable method and a series of discrete bonds are represented by numeral 46. Also indicated are autogenous bonds at 48 which bond the flaps 26 and 28 to the outer cover. As can be appreciated, the folding of the flaps 26 and 28 over the ends of absorbent structure 22 maintains absorbent structure 22 in position in relation to outer cover 20 without inhibiting the stretchability of outer cover 20. FIG. 5 is a sectional view of cross section 5—5 of FIG. 4 and shows the relationship of waist flap 26 when folded over absorbent structure 22. It is to be especially noted that there are no direct bonds holding the ends of absorbent structure 22 to either the outer cover 20 or to waist flaps 26 or 28. This ensures that the stretchability of outer cover 20 is uninhibited by absorbent structure 22. In addition to front and back waist flaps 26 and 28 there are autogenous bonds, indicated at 50, bonding absorbent structure 22 to outer cover 20 in the crotch section of the diaper. Although these bonds may inhibit the stretchability of the crotch section of outer cover 20, the bonds do not inhibit the functionality of outer cover 20 since there is minimal need for outer cover 20 to be stretched in a cross body direction in the crotch area.

Figure 7:
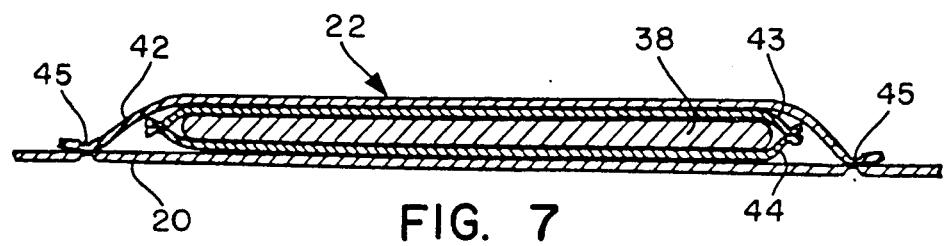
FIG. 7 is a sectional view of cross section 7—7 shown in FIG. 6.
Figure 8:
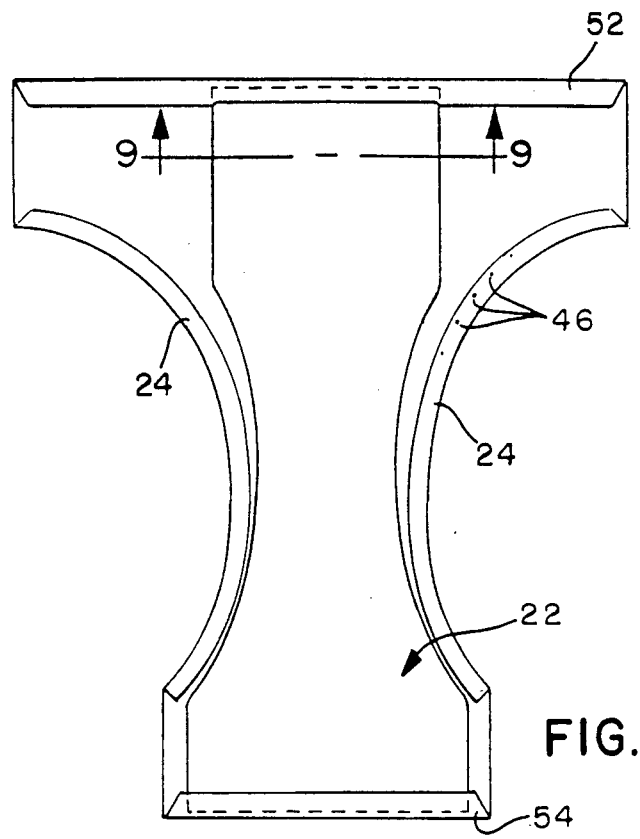
FIG. 8 is the alternative embodiment shown in FIG. 6 in a finished condition.
Figure 9:
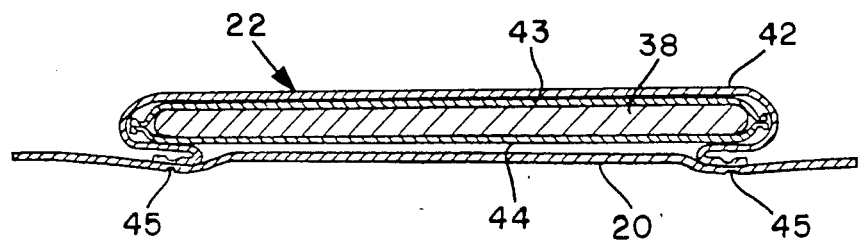
FIG. 9 is a sectional view of cross section 9—9 as shown in FIG. 8.

FIGS. 6-9 illustrates an alternative embodiment of the disposable diaper of the present invention. Referring to FIGS. 6-9 together, it is seen that absorbent structure 22 comprises a bodyside liner 42, a liquid impermeable barrier 44 with an absorbent composite 38 disposed therebetween. As shown in FIG. 7, which is a sectional view of cross section 7—7 of FIG. 6, the bodyside liner 42 is bonded to outer cover 20 rather than to barrier 44 as disclosed in the previous embodiment. In order to maintain the shape of absorbent composite 38 during manufacture the absorbent composite may be wrapped with tissue or have a tissue 43 bonded to barrier 44 as shown in FIGS. 7 and 9. The bodyside liner 42 is bonded to outer cover 20 when outer cover 20 is in a stretched condition. Bodyside liner 42 may be bonded to outer cover 20 by any conventional method with the preferable method being autogenous bonding as discussed hereinabove and indicated generally at 45. FIGS. 8 and 9 show the disposable diaper shown in FIGS. 6 and 7 when outer cover 20 is in an unstretched condition. It is noted that the figures are not meant to be dimensionally accurate. Referring especially to FIG. 9, which is a sectional view of cross section 9—9 in FIG. 8, it can be seen that when outer cover 20 is relaxed, after bodyside liner 42 is bonded to it, bodyside liner 42 is drawn under absorbent structure 22 by outer cover 20, and as can be appreciated, this method does not inhibit the stretchability of outer cover 20. The disposable diaper illustrated in FIGS. 6 through 9 has a relatively narrow hem 52 at the back waist section and a relatively narrow hem 54 at the front waist section rather than the wider hems made by waist flaps 26 and 28 illustrated in FIGS. 2 through 5.

Figure 10:
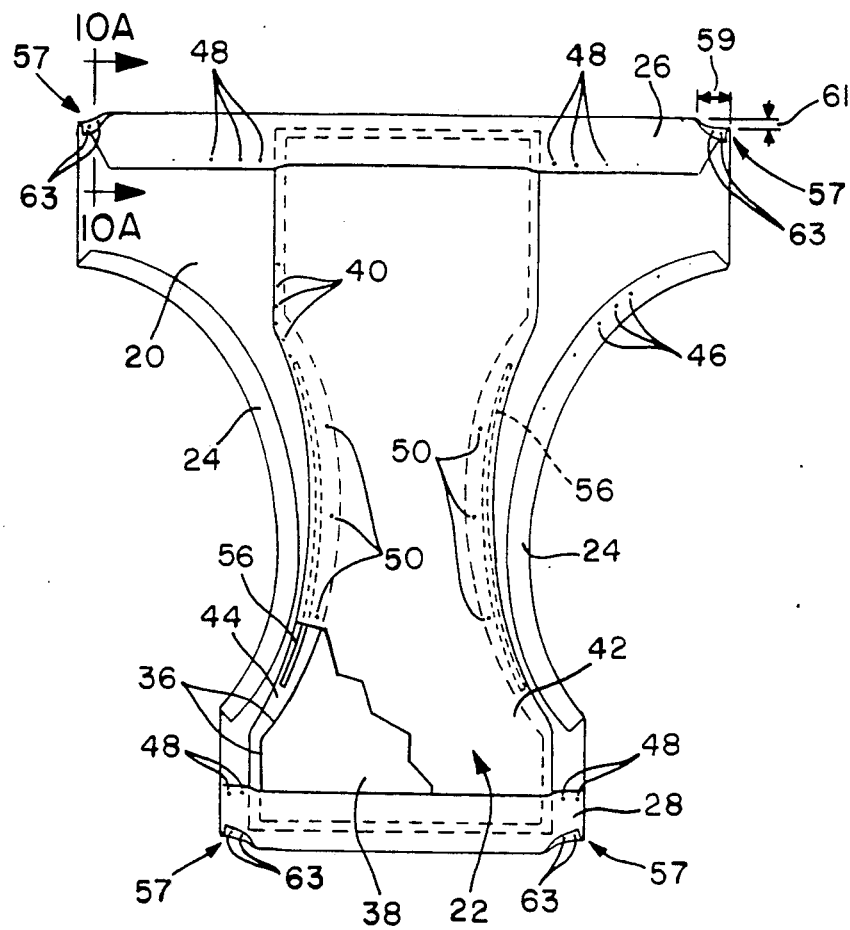
FIG. 10 is a plan view of a further alternative embodiment of the disposable diaper of the present invention.
Figure 10A:
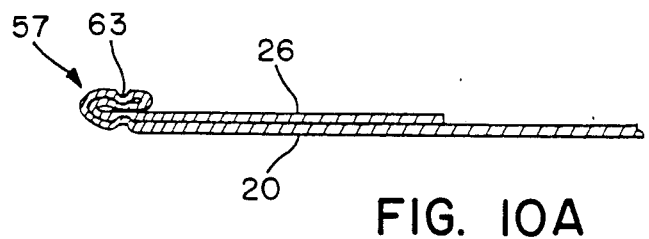
FIG. 10A is a sectional view of cross section 10A—10A as shown in FIG. 10.

FIG. 10 illustrates a further alternative embodiment of the disposable diaper of the present invention in which elastic members 56 are shown disposed within the crotch section of absorbent structure 22. Elastic members 56 are adhesively bonded to either bodyside liner 42 or to barrier 44. It is preferable that elastic members 56 are bonded to bodyside liner 42 because absorbent structure 22 is caused to form a cupped shape by the tension of elastic members 56 when the diaper is placed on an infant. Autogenous bonds 40 which bond bodyside liner 42 to barrier 44 are shown only partially in FIG. 10 as are autogenous bonds 48. It is noted that autogenous bonds 50 which bond absorbent structure 22 to outer cover 20 are shown inside elastic member 56. Also illustrated in FIGS. 10 and 10A are waist tucks 57 on the outermost sections of back waist flap 26 and front waist flap 28. The waist tucks 57 cause the waist to appear straight across when the diaper is secured around a baby and provide a smooth contour near the fastener position. The waist tucks 57 are situated near the extreme edges of front and back waist flaps 26 and 28, respectively, to be folded over as shown more clearly in FIG. 10A, which is a sectional view of cross section 10A—10A as shown in FIG. 10. The distance represented at 59 is in the range of from $\frac{1}{4}$ inch to $\frac{1}{2}$ inch and the fold distance, represented at 61 is approximately $\frac{1}{4}$ inch. In addition to causing the waist to appear straight across the baby, the waist tucks 57 cause the waist to stay closer to the baby thereby eliminating any tendency for the waist to gap. Without the gapping the appearance of the diaper on the baby is improved and the waist area fits more snugly without adding undue tension to the waist area. The waist tucks are preferably held in place by autogenous bonds indicated at 63. As discussed hereinabove, over bonding methods may be utilized and are to be considered within the scope of the present invention.

Figure 11:
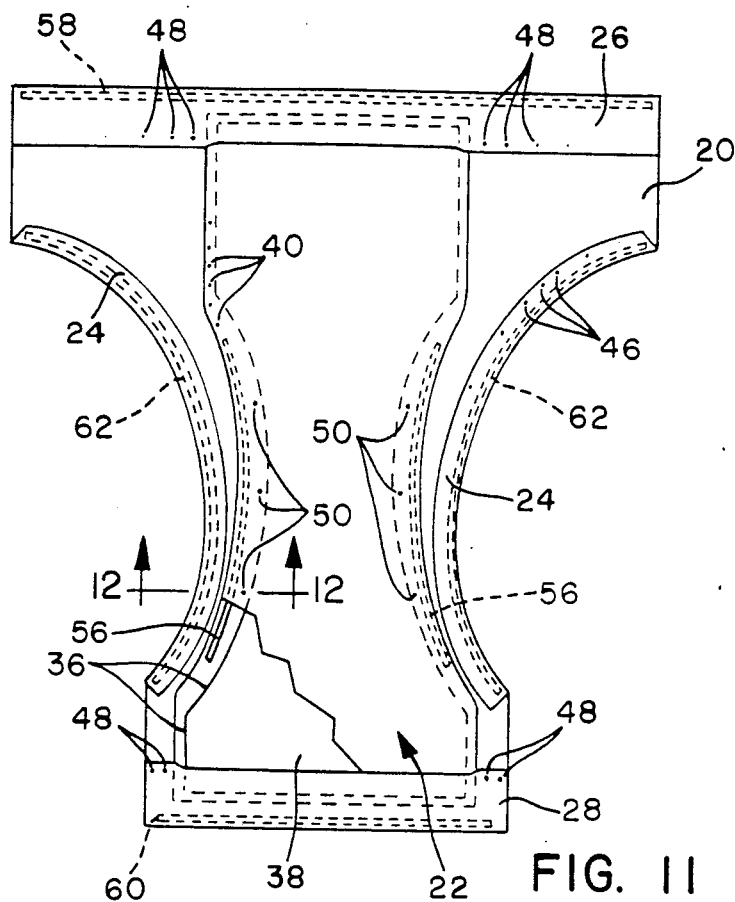
FIG. 11 is a plan view of a still further alternative embodiment of the disposable diaper of the present invention.
Figure 12:
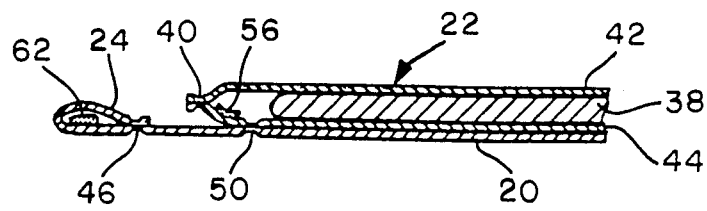
FIG. 12 is a sectional view of cross section 12—12 as shown in FIG. 11.

FIGS. 11 and 12 illustrate a still further embodiment of the disposable diaper of the present invention wherein an elastic member 58 is disposed within back waist flap 26 and an elastic member 60 is disposed within front waist flap 28. Also, elastic members shown in 62 are disposed in leg hems 24. FIG. 12 is a sectional view of cross section 12—12 shown in FIG. 11 and shows the disposition of elastic members 56 and 62 in the absorbent structure 22 and leg hems 24 respectively. As indicated earlier, autogenous bonds 50 bond liquid impermeable barrier 44 to outer cover 20 while autogenous bonds 40 bond liquid permeable layer 42 to liquid impermeable layer 44 of the absorbent structure with absorbent composite 38 disposed therebetween. Also shown in FIG. 12 are autogenous bonds 46 bonding hems 24 to outer cover 20 with elastic members 62 disposed within hems 24. It is noted that hems 24 are made up of portions of outer cover 20.

Figure 13:
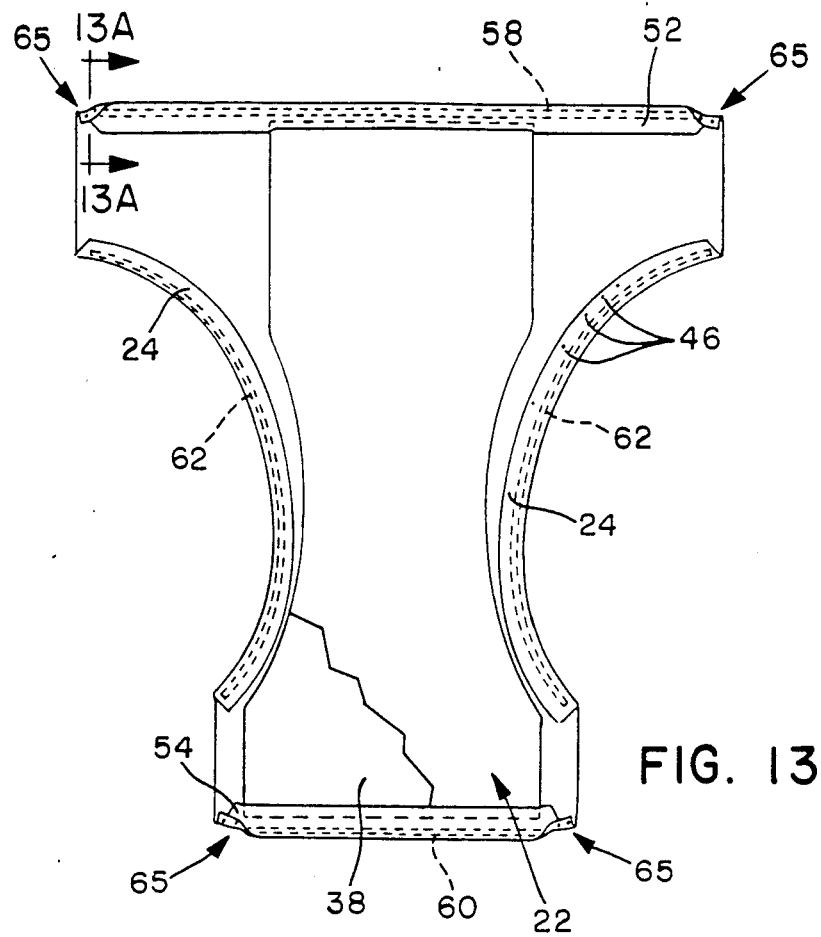
FIG. 13 is still another alternative embodiment of the disposable diaper of the present invention.
Figure 13A:
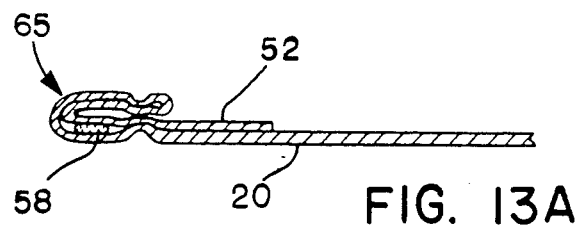
FIG. 13A is a sectional view of cross section 13A—13A as shown in FIG. 13.

FIGS. 13 and 13A show the disposable diaper shown in FIGS. 6 through 9 with elastic member 58 disposed in hem 52, elastic member 60 disposed in hem 54 and elastic members 62 disposed in leg hems 24. FIG. 13A which is a sectional view of cross section 13A—13A as shown in FIG. 13 illustrates waist tucks 65 similar to the waist tucks 57 described in the discussion relating to FIGS. 10 and 10A. The tucks 65 shown in FIGS. 13 and 13A are shown folded and including the elastic member 58. This serves to anchor the elastic member 58. Further discussion concerning the anchoring of elastic members will be presented relating to FIG. 19.

Figure 14:
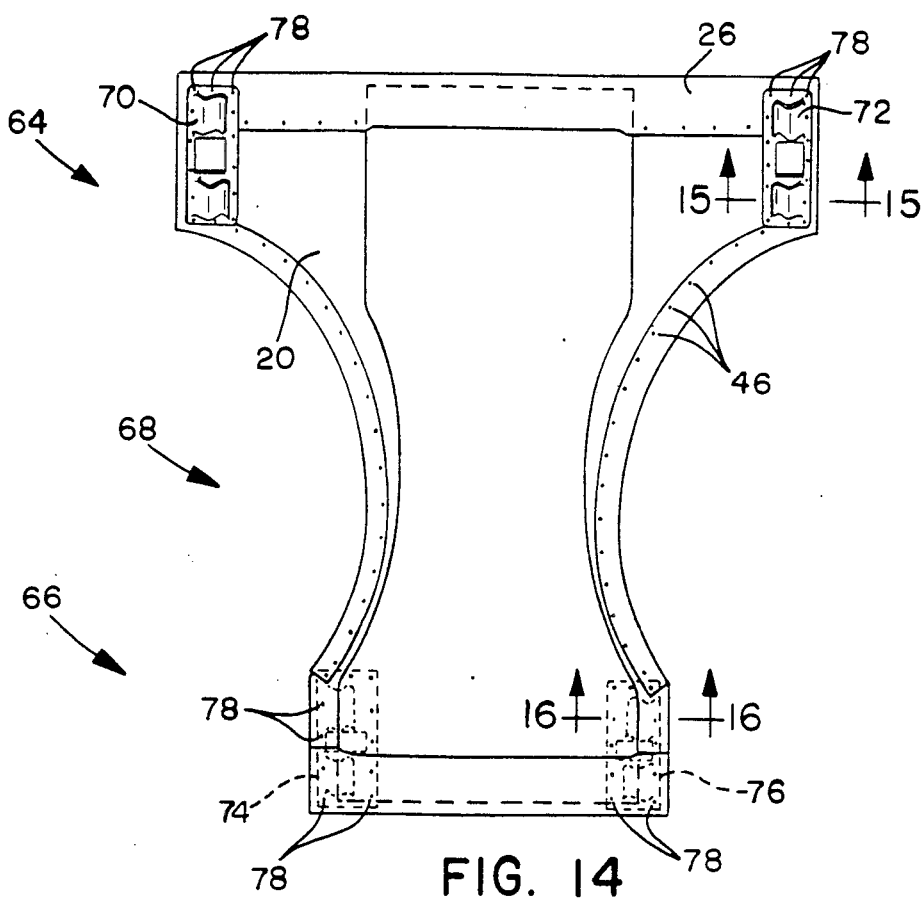
FIG. 14 is a plan view of an embodiment of the disposable diaper of the present invention showing a first method of attaching fixed position fasteners to the diaper.
Figure 15:
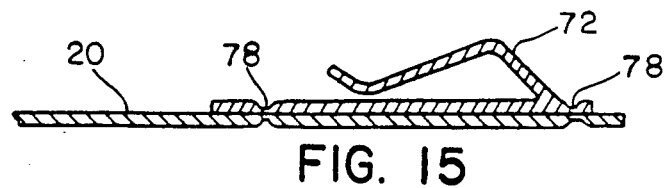
FIG. 15 is a sectional view of cross section 15—15 as shown in FIG. 14.
Figure 16:
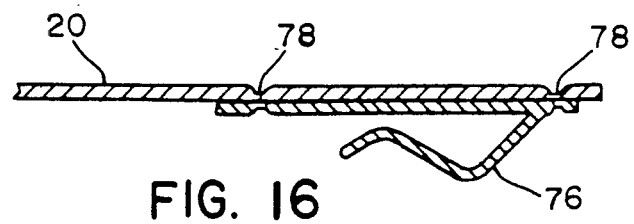
FIG. 16 is a sectional view of cross section 16—16 as shown in FIG. 14.

FIGS. 14 through 16 illustrate an embodiment of fixed point fasteners attached to outer cover 20. Outer cover 20 is generally made up of a back waist section 64, a front waist section 66 and a crotch section 68 disposed therebetween. Attached to outermost portions of backwaist section 64 are a pair of fastener members 70 and 72 which will be discussed in more detail in conjunction with a later figure. Attached to outermost portions of front waist section 66 are a pair of fastener members 74 and 76 which will also be discussed in more detail in conjunction with a later figure. It is noted that fastener members 70 and 72 are attached to the inner side of outer cover 20 while fastener members 74 and 76 are attached to the outer side of outer cover 20. It is further noted that fastener members 70 and 72 could be fastened to the outer side of outer cover 20 and fastener member 74 and 76 could be attached to the inner side of outer cover 20. FIG. 14 shows the fastener members 70, 72, 74 and 76 attached to outer cover 20 with autogenous bonds represented at 78. FIG. 15 is a sectional view of cross section 15—15 shown in FIG. 14 and shows fastener member 72 attached to outer cover 20 with autogenous bonds 78 (shown partially). It should be appreciated that other methods of bonding fastener member 72 to outer cover 20 are comprehended and the illustration of autogenous bonds is not meant to be limiting. FIG. 16 is a sectional view of cross section 16—16 of FIG. 14 and shows fastener member 76 bonded to outer cover 20 by autogenous bonds 78. Similarly it is noted that other methods of bonding fastener member 76 to outer cover 20 could be utilized. FIGS. 14 through 16 illustrate a method wherein when the pair of fasteners 70 and 72 are interlocked with the pair of fasteners 74 and 76, the outermost portions of backwaist section 64 overlap front waist section 66. This overlapping fastening method will be seen more clearly in relation to FIGS. 17 and 18.

Figure 17:
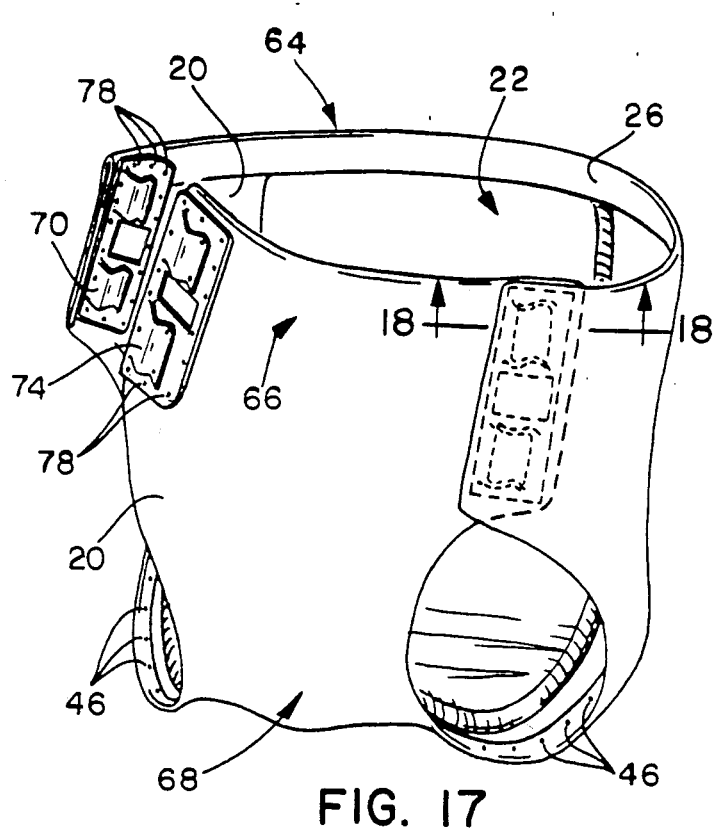
FIG. 17 is a perspective view of an embodiment of the disposable diaper of the present invention as it would be secured around a wearer.
Figure 18:
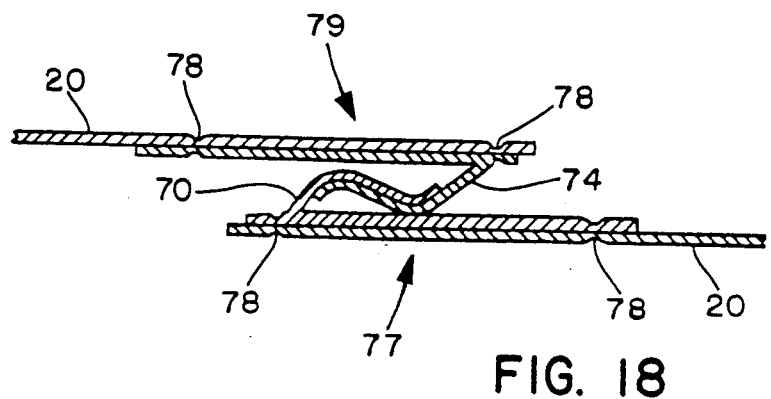
FIG. 18 is a sectional view of cross section 18—18 as shown in FIG. 17.

Referring now to FIGS. 17 and 18, FIG. 17 illustrates a diaper as it would be secured around a baby with one fastener open to illustrate its relative position. FIG. 18 is a sectional view of cross section 18—18 of FIG. 17 and shows fastener members 70 and 74 interlocked with fastener member 70 bonded with autogenous bonds represented at 78 to outer cover 20 and fastener member 74 attached to outer cover 20 with autogenous bonds 78. It is noted that a first portion of outer cover 20 indicated at 77 overlaps a second portion of outer cover 20, indicated at 79.

Figure 19:
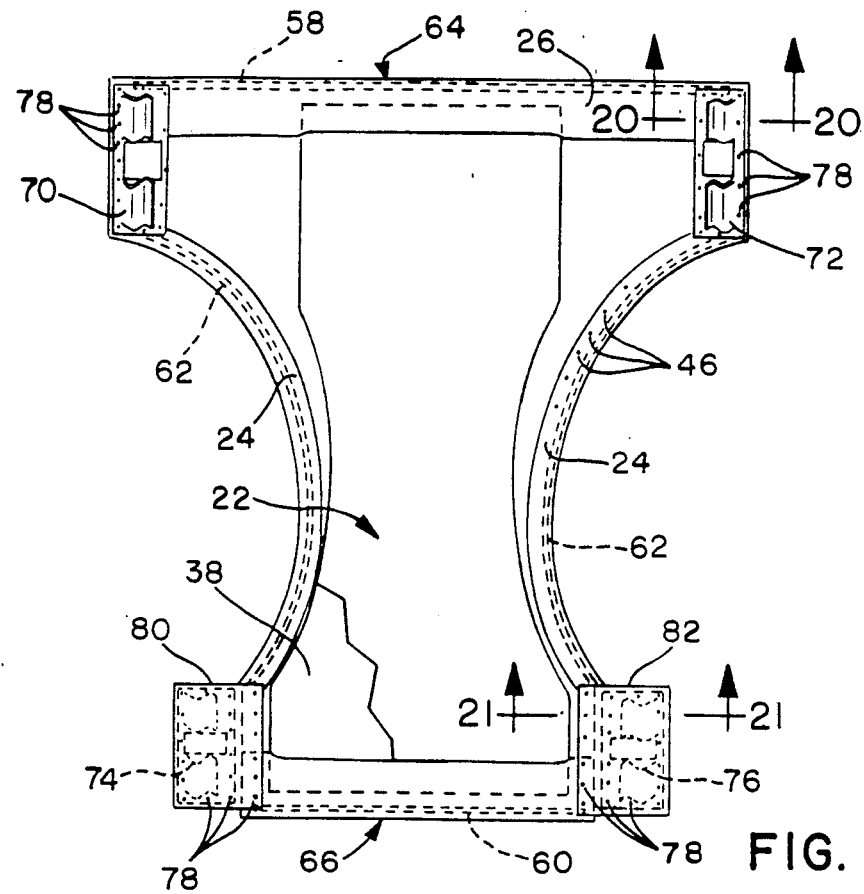
FIG. 19 is a plan view of the disposable diaper of the present invention showing a second method of attaching the fixed position fasteners to the diaper.
Figure 20:
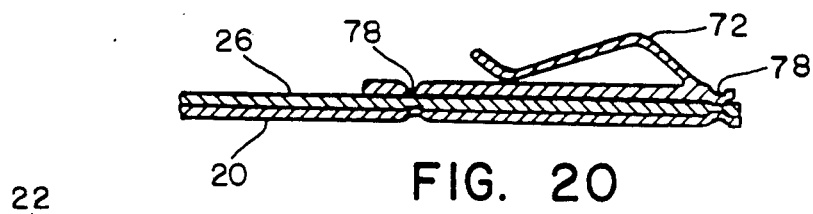
FIG. 20 is a sectional view of cross section 20—20 as shown in FIG. 19.
Figure 21:
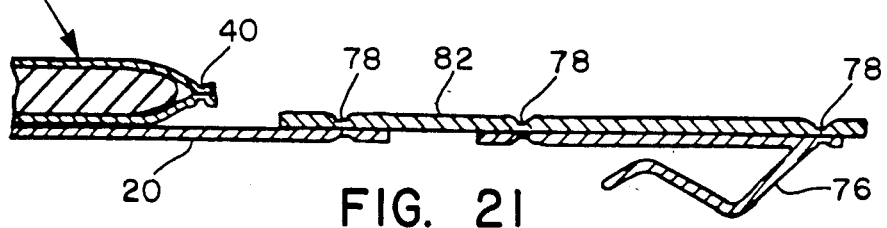
FIG. 21 is a sectional view of cross section 21—21 as shown in FIG. 19.

Referring now to FIGS. 19, 20, and 21 there is illustrated another embodiment of the disposable diaper of the present invention. In this embodiment, outer cover extension members 80 and 82 are attached to outermost portions of front waist section 66. Fastener members 74 and 76 are attached to extension members 80 and 82. As above, the methods of attaching extension members 80 and 82 to outermost portions of front waist section 66 of outer cover 20 and the fastener members 74 and 76 to the extension members 80 and 82 can be of several known methods in the art including adhesives, stapling, riveting, sewing, etc. Shown in this embodiment is autogenous bonding illustrated graphically by dots 78 relating to the attachment of the fastener members 70, 72, 74, 76 to the extension members 80, 82 and the attachment of the extension members 80, 82 to the outer cover 20.

Also shown in FIGS. 19, 20 and 21 is the aspect of imparting elasticity to the waist sections and leg hems. One method of imparting elasticity is by utilizing elastic members 58 and 60 in the waist sections and elastic members 62 in the leg hems 24. It should be understood that the elastic members 58, 60, 62 may be utilized in any of the embodiments of the present invention, but have been shown in only selected figures for the sake of clarity. The elastic members may comprise any of the usual elastics utilized in the diaper making art such as a thin ribbon of natural rubber, etc. A preferred method of imparting elasticity to the waist sections and/or the leg hems is by extruding a hot melt pressure-sensitive elastomeric adhesive such as that marketed by H. B. Fuller Co. of St. Paul, Minn., U.S.A. under the trademark FULLASTIC. It is to be noted that in FIG. 19 the waist elastic members are shown anchored at each end by respective fastener members. For example, elastic member 58 is anchored at each end by fastener members 70 and 72. In addition, as discussed above in relation to FIG. 13 elastic members in the waist may be anchored by tucks 65. Similarly, elastic member 60 is anchored at each end by fastener members 74 and 76. Both leg elastic members 62 are also anchored by the respective fastener members. The anchoring of the elastic members provides for a more even distribution of force thereby precluding destruction or unattractive tensioning of any one portion of the diaper. This aids in the prevention of gapping thereby aiding in eliminating the leakage of urine and feces.

Figure 22:
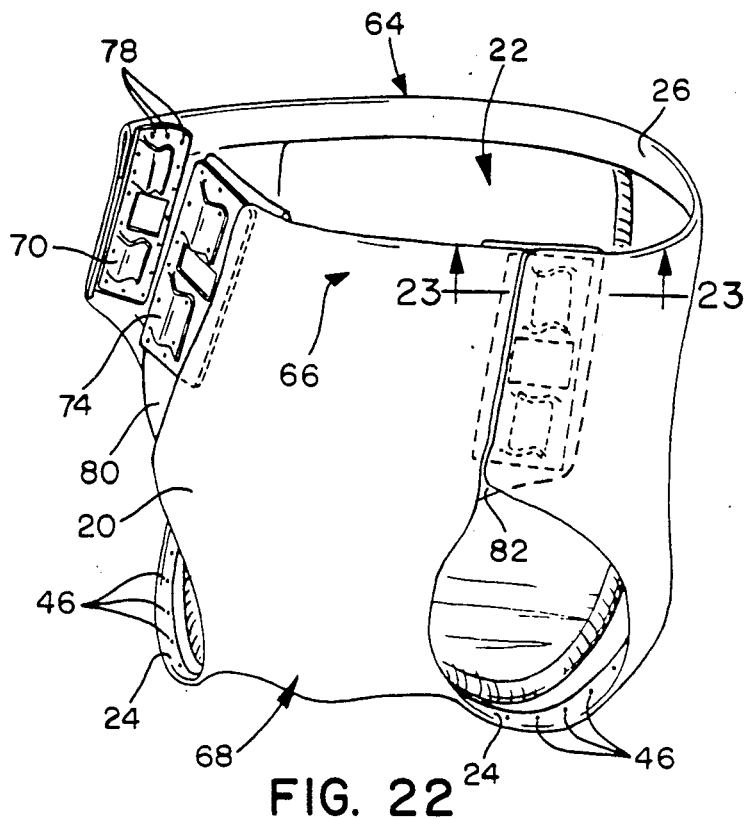
FIG. 22 is a perspective view of an embodiment of the disposable diaper of the present invention as it would be secured around a wearer.
Figure 23:
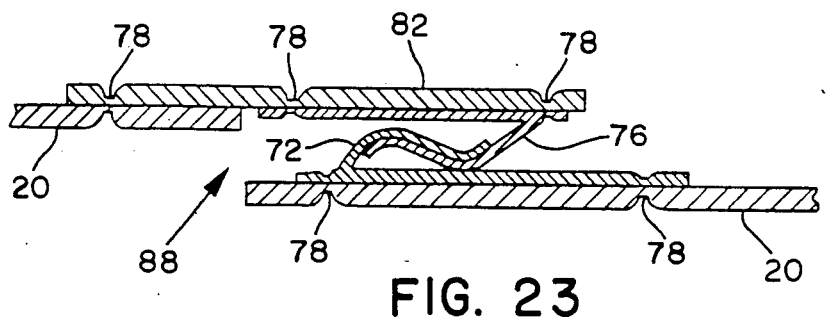
FIG. 23 is a sectional view of cross section 23—23 as shown in FIG. 22.

FIG. 22 illustrates the embodiment shown in FIGS. 19-21 as it would appear on a child with one fastener open to show the relationship of the fastener members. FIG. 23 is a sectional view of cross section 23—23 of FIG. 22. FIG. 23 illustrates graphically the butt splice at 88 that results from the addition of extension members 80, 82. Note at 88 that the two portions of outer cover 20 meet without overlapping.

Figure 24:
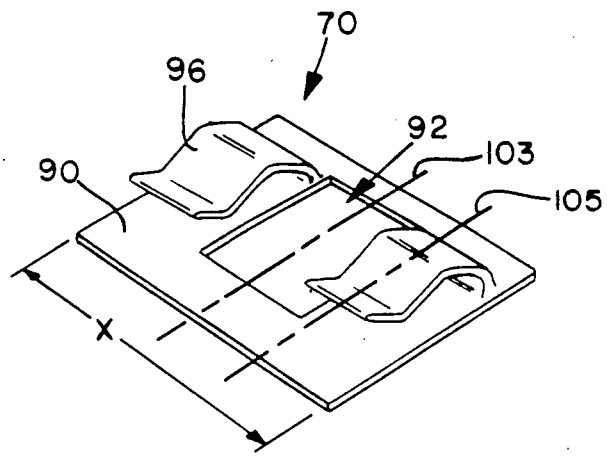
FIG. 24 is a perspective view of one member of the fixed position fastener.
Figure 25:
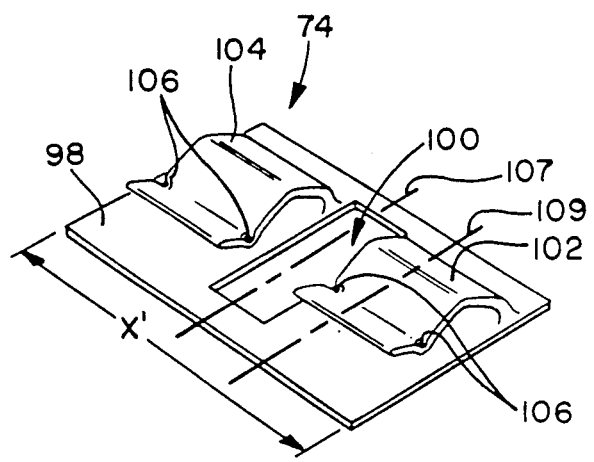
FIG. 25 is a perspective view of a second member of the fixed position fastener.

FIGS. 24 and 25 illustrate an embodiment of the fixed position fastener members 70 and 74 respectively. It is anticipated that fastener members 70,74 can be manufactured by several methods. One method to efficiently produce fastener members 70,74 is to design the members so that they can be extruded in a substantial length whereby individual members can be cut from the substantial length of material. The substantial length can be rolled and stored for subsequent processing. A further aspect of efficient production is to design the fastener members to have the same cross section so that each fastener member can be cut from the same roll of material.

It has been determined that the fastener members 70,74 must be carefully designed and made from a carefully selected material so that they do not cause the baby's skin to be chafed or irritated and at the same time do not come unfastened easily. Another factor that must be considered in the selection of the material for fastener members 70,74 is the method of attachment to the garment or the method by which the fastener members 70,74 are to be integrated with the garment. For example, if autogenous bonding is to be utilized, it would be necessary to select a material that is autogenously bondable.

A selection criterion for the selection of a material and design for fastener members 70,74 is to consider the Moment of Inertia (I) of the material in conjunction with the Modulus of Elasticity (E). This selection criterion which involves the product of (E)(I) is utilized as follows. The value (E)(I) is determined in a material/-design combination, that is, the value (E)(I) is determined for a particular design utilizing a particular material. The value (E)(I) is calculated from the following formula taken from the textbook "Mechanical Engineering Design," 2nd Ed. by Joseph E. Shigley, Published by McGraw-Hill, 1972, page 699.

$$EI = L^3 M/48$$

wherein M is obtained from ASTM test D-790 and wherein L is defined by ASTM test D-790.

It has been determined, for example, for fastener members such as fastener members 70,74 that a material/design combination with (E)(I) in the range of about 0.5 pound-inches$^2$ to about 3.5 pound-inches$^2$ is preferable in that the fastener members 70,74 when mated or connected do not chafe the skin of the wearer under normal usage and normal conditions and do not easily come unfastened under normal usage and normal conditions. A particularly preferable range of values of (E)(I) is from about 0.9 pound-inches$^2$ to about 3.4 pound-inches$^2$.

The Modulus of Elasticity (E) can be determined for various materials from standard tables. It has been found that if a material is selected having a Modulus of Elasticity in the range of about 4,000 psi to about 60,000 psi and more preferably in the range of about 6,000 psi to about 40,000 psi the attaining of a satisfactory value of (E) (I) is facilitated. Table 1 lists representative materials and their Moduli of Elasticity.

TABLE 1

| MATERIAL | MODULUS OF ELASTICITY (psi) |
|---|---|
| 65% Dow 722 35% PP PROFAX* 7823 | 28,900–40,400 " |
| 50% DOW 722 35% PP PROFAX 7823 | 71,000–89,000 " |
| 50% EVA (ethylene vinyl acetate) 50% PP PROFAX 7823 | 54,000–55,600 " |
| Injection Molded PP PROFAX 7823 | 46,000 |
| POLYURETHANE ESTANE** 58134 | 9,000 |
| POLYURETHANE ESTANE 58130 | 18,000 |
| POLYURETHANE ESTANE 58133 | 22,100 |
| POLYURETHANE ESTANE 58810 | 12,000 |

*PROFAX is a tradename of Hercules Co.
**ESTANE is a tradename of B. F. Goodrich As can be appreciated, the proper selection of a fastener material in conjunction with the proper design of a fastener member is of permanent importance for the comfort and functionality of the garment. If the fastener material is too inflexible it may cause discomfort and possible injury to the wearer. If the fastener material is too flexible, it may be difficult to fasten, it may not remain fastened under normal usage and normal conditions and it may not maintain the shape of the garment, that is, it may allow the garment to roll or bunch up.

Referring again to FIG. 24, the fastener member 70 is comprised generally of a flat portion 20, an aperture 92 and two configured clasps 94, 96. The fastener member 70 as shown in FIG. 24 is obtained by cutting a section with a length "x" from the continuous roll of material as described above. The cross section of the entire length "x" of the section would be that as indicated by line 105. The aperture 92 is then provided which removes a portion of material from flat portion 90 and a portion of the clasp material which would be between clasp 94 and 96.

Referring now to FIG. 25 there is shown fastener member 74 (fastener member 76 is the same). Fastener member 74 is made in a similar way to that described above for fastener member 70. The fastener member 74 is cut from a continuous roll of material (not shown). This roll of material can be, and it is preferable, that the same roll of material that fastener member 70 is cut from be used. In this case the member 74 is comprised generally of a flat portion 98, an aperture 100 and two clasps 102 and 104. The section is cut with a length "x'" which is longer than the length "x" of fastener members 70, the reason for which will become apparent. In addition, as is shown in FIG. 25, the length of aperture 100 is smaller than aperture 92 shown in FIG. 24. The ends of clasps 102 and 104 are sufficiently larger than the ends of clasps 94 and 96 to allow ends of clasps 94 and 96 to interlock under clasps 102 and 104. The sides of clasps 102 and 104 may be bonded to flat portion 98 as indicated at 106. A preferable method of bonding is by autogenous bonding and autogenous bonds are indicated at 106.

Referring to FIGS. 24 and 25 and to the discussion relating to the values of EI above, the values of EI through the areas indicated by line 105 (FIG. 24) and line 109 (FIG. 25) are selected to be in the range of 0.5–3.5 pound-inches$^2$ and preferably in the range of 0.9–3.4 pound-inches$^2$. The values of EI through the areas indicated by line 103 (FIG. 24) and line 107 (FIG. 25) is selected to be in the range of 0.002 to 0.010 pound-inches$^2$.

Referring to FIG. 26 there is shown invididual clasps 102 and 94 interlocked. The interrelationship of the clasps and the required relationship of lengths "x" (FIG. 24) and "x'" (FIG. 25) is now apparent. The fasteners members have a complementary cross section for mating engagement and are releasably interlockable. The autogenous bonds 106 bonding the edge of clasp 102 to flat area 98 serve a twofold purpose; one, to provide stability to the fasteners and two, to prevent clasp 94 from sliding out from the side of clasp 102.

Turning now to a description of the materials used for the various components, it is desirable that the liquid permeable bodyside liner 42 utilized in the disposable diaper of the present invention meet the following criteria. One, the bodyside liner 42 should be dry, i.e., be and feel dry when the absorbent structure 22 is loaded with urine. A measure of this criterion is that the bodyside liner 42 feel dry to the touch after a normal urine loading of the absorbent structure. Two, the z-direction (defined as the direction from the bodyside liner outward to the outer cover) fluid penetration rate of bodyside liner 42 should be high enough to allow urine to penetrate through to the absorbent composite at an infant's urination rate. Three, the feel, color and opacity are further criteria that are most preferably satisfied by a white material, although other colors may be acceptable, with an opacity sufficient to mask the color of urine or feces within the absorbent composite. Four, bodyside liner 42 should be autogenously bondable to liquid impermeable barrier 44. Barrier 44 is preferably made from polypropylene, however, other liquid impermeable materials can be used.

The bodyside liner is a soft, compressible material comprised of synthetic fibers such as polyester/polypropylene integrally bonded to a top liner at spaced apart sites to provide densified zones for fluid transfer. Such a web is described in U.S. Pat. No. 4,397,644, issued to Mattews et al. and assigned to the assignee of the present application, the disclosure of which is incorporated herein by reference and relied upon. The top liner is a pattern bonded spunbonded web also of synthetic fibers such as polypropylene, polyester and the like. The combined basis weight of the bodyside liner should be in the range of about 30–100 g/m$^2$. It should have a wetting finish throughout. The bottom layer of the bodyside liner is typically a carded web of polyester/polypropylene fiber containing up to 100% polyester fiber, preferably 25–50% polyester staple, containing sufficient surfactant finish to be wettable. Two-inch polyester stape, Type T808, a hollow fiber, at 5.5 denier from E. I. duPont Co. with a wettable finish is preferred although other wettable polyester staple fibers would work. Polypropylene Type T-123 from Hercules Inc. has a wettable finish with the 3-denier, 1½ inch staple preferred. The web is only bonded together through the spaced apart bonds which attach is to the liner, which are typically achieved through thermal or ultrasonic bonding. The bottom layer may also be formed by other nonwoven processes such as spunbonding in which the filaments are spuns and collected on a wire screen without bonding and then bonded to the prebonded liner as described above. It should have a wetting finish, for example, as is achieved by treating with 0.2–0.5% TRITON X-102 from Rohm and Haas Co., or equivalent surfactant.

The outer cover 20 of the present invention is preferably made from a resiliently stretchable material having a stretchability of from about 20 percent to about 200 percent. The term stretchability as used herein is defined by the following relationship:

stretchability = ((final dimension − initial dimension)/initial dimension) × 100%

The outer cover 20 is also resilient, that is, the outer cover returns essentially to its initial dimension when the stretching force is removed.

One such resiliently stretchable material is disclosed in U.S. patent application, Ser. No. 760,698 in the name of Tony J. Wisneski and Michael T. Morman, assigned to the assignee of the present application, entitled "Polyolefin-containing Extrudable Compositions and Methods for their Formation Into Elastomeric Products", the disclosure of which is incorporated herein by reference and relied upon. That application provides extrudable elastomeric compositions which, after extrusion, solidify to form elastomeric products such as, for example, fibrous nonwoven elastomerics webs. As used herein and in the referenced pending application, the term 'nonwoven web' means a web of material which has been formed without use of weaving processes which produce a structure of individual fibers or threads which are interwoven in an identifiable repeating manner. Nonwoven webs have been, in the past, formed by a variety of processes such as, for example, meltblowing processes, spunbonding processes, film aperturing processes and staple fiber carding processes. The extrudable elastomeric compositions are blends of (1) from at least about 10 percent, by weight, of an A-B-A' block copolymer, where "A" and "A'" are each a thermoplastic polymer endblock which includes a styrenic moiety such as a poly(vinyl arene) and where "B" is an elastomeric poly(ethylene-butylene) midblock, with (2) from greater than 0 percent, by weight, to about 90 percent, by weight, of a polyolefin which, when blended with the A-B-A' block copolymer and subjected to appropriate elevated pressure and elevated temperature conditions, is extrudable, in blended form, with the A-B-A' block copolymer. The A-B-A' block copolymer serves to impart elastomeric properties to products formed from the extrudable composition and the presence of the polyolefin in the blend serves to reduce the viscosity of the composition as compared to the viscosity of the neat, that is, pure, A-B-A' block copolymer and thus enhances the extrudability of the composition.

Preferably, the "A"0 and "A'" thermoplastic styrenic moiety containing endblocks of the block copolymer are selected from the group including polystyrene and polystyrene homologs such as, for example, poly(alphamethylstyrene). In some embodiments the "A" and "A'" thermoplastic styrenic moiety containing endblocks are identical. Preferably, the polyolefin is selected from the group including at least one polymer selected from the group including polyethylene, polypropylene, polybutene, ethylene copolymers, propylene copolymers, butene copolymers or blends of two or more of these materials.

The blend usually includes from at least about 20 percent, by weight, to about 95 percent, by weight, of the block copolymer and from at least about 5 percent, by weight, to about 80 percent, by weight, of the polyolefin. For example, the blend may include from about 30 percent, by weight, to about 90 percent, by weight, of the block copolymer and from about 10 percent, by weight, to about 70 percent, by weight, of the polyolefin. Preferably, the blend includes from about 50 percent, by weight, to about 90 percent, by weight, of the block copolymer and from about 10 percent, by weight, to about 50 percent, by weight, of the polyolefin. For example, the blend may include from about 50 percent, by weight, to about 70 percent, by weight, of the block copolymer and from about 30 percent, by weight, to about 50 percent, by weight of the polyolefin. One blend includes about 60 percent, by weight, of the polyolefin.

The extrudable composition is extruded or otherwise formed, such as, for example, by molding, for example, injection molding, at an appropriate, that is effective, combination of elevated pressure and elevated temperature conditions. These conditions will vary depending on the polyolefin utilized. For example, the extrudable composition should be extruded or otherwise formed at a temperature of at least about 125 degrees Centigrade if polyethylene is utilized as the polyolefin in the blend or at least about 175 degrees Centigrade if polypropylene is utilized in the blend, for example, at a temperature of from at least about 290 degrees Centigrade to about 345 degrees Centigrade, more specifically, at a temperature of from at least about 300 degrees Centigrade to about 335 degrees Centigrade, into elastomeric products such as, for example, elastomeric fibers, which may be collected as a fibrous nonwoven elastomeric web.

Preferably the blends are extrudable within the above-defined temperature ranges at elevated pressures within the die tip, (for example, within the extrusion capillaries of a die tip having thirty (30) extrusion capillaries per lineal inch of die tip with each of the capillaries having a diameter of 0.0145 inches and a length of 0.113 inches) of no more than about 300 pounds per square inch, gage, for example, from pressures of from about 20 pounds per square inch, gage, to about 250 pounds per square inch, gage. More specifically, the blends are extrudable within the above-defined temperature ranges at pressures and from about 50 pounds per square inch, gage, to about 250 pounds per square inch, gage, for example, from about 125 pounds per square inch, gage, to about 225 pounds per square inch, gage. Higher elevated pressures can be utilized with other die designs having a lower number of capillaries per inch of die, but, generally speaking, lower production rates result.

Importantly, it has been found that the extrudable compositions are extrudable at satisfactory throughput rates because the presence of the polyolefin in the extrudable composition reduces the viscosity of the extrudable composition, as compared to the viscosity of the neat, that is, pure, block copolymer, to satisfactory levels. This reduced viscosity proportionally reduces the die tip pressure if all other parameters remain the same. For example, the viscosity of the extrudable compositions will generally be less than about 500 poise when extruded at the above-defined elevated temperature and elevated pressure ranges. Preferably, the viscosity of the extrudable composition is less than about 300 poise when extruded at the above-defined elevated temperatures and elevated pressure ranges. For example, the viscosity of the extrudable composition may be from at least about 100 poise to about 200 poise when extruded at the above-identified elevated temperature and elevated pressure conditions.

Because the polyolefin reduces the viscosity of the blend, as compared to the viscosity of the block copolymer, the extrudable composition is extrudable within the above-identified elevated temperature and elevated pressure ranges, through a die tip having, for example, thirty capillaries per inch of die tip with the capillaries having a diameter of about 0.0145 inches and a length of about 0.113 inches at a rate of from at least about 0.02 grams per capillary per minute to about 1.7 or more grams per capillary per minute. For example, the extrudable composition may be extruded through the above-identified die tip having capillaries with a diameter of about 0.0145 inches and a length of about 0.113 inches at the rate of from at least about 0.1 grams per capillary per minute to about 1.25 grams per capillary per minute. Preferably, the extrudable composition is extrudable through the above-identified die tip having capillaries with a diameter of about 0.0145 inches and a length of about 0.113 inches at the rate of from at least about 0.3 grams per capillary per minute to about 1.1 grams per capillary per minute.

The extrudable composition may be formed into fibrous nonwoven elastomeric webs preferably having microfibers with an average diameter of not greater than about 100 microns, and preferably having an average basis weight of not more than about 300 grams per square meter, for example, an average basis weight of from about 5 grams per square meter to about 100 grams or more per square meter. More specifically, an average basis weight of from about 10 grams per square meter to about 75 grams per square meter. For example, a fibrous nonwoven elastomeric web may be formed by extruding the extrudable composition at an appropriate, that is, effective, combination of elevated temperature and elevated pressure conditions. Preferably, the extrudable composition is extruded at a temperature of from at least about 125 degrees Centigrade if the polyolefin is polyethylene or at least about 175 degrees Centigrade if the polyolefin is polypropylene, for example, from about 290 degrees Centigrade to about 345 degrees Centigrade, more specifically from about 300 degrees Centigrade to about 335 degrees Centigrade. Preferably, the extrudable composition is extruded within the above-identified temperature ranges and pressures, within the die tip, (for example, within the extrusion capillaries of a die tip having thirty (30) extrusion capillaries per lineal inch of die tip with each of the capillaries having a diameter of about 0.0145 inches and a length of 0.113 inches) of no more than about 300 pounds per square inch, gage, for example, from about 20 pounds per square inch, gage, to about 250 pounds per square inch, gage. More specifically, the extrudable composition is extruded at a pressure within the capillaries of the above-identified die tip of from about 50 pounds per square inch, gage, to about 250 pounds per square inch, gage, for example, from about 125 pounds per square inch, gage, to about 225 pounds per square inch, gage.

In the formation of elastomeric nonwoven webs, the extrudable composition is extruded, at the above-defined elevated temperature and elevated pressure conditions at a rate of from at least about 0.02 gram per capillary per minute to about 1.7 or more grams per capillary per minute, for example, from at least about 0.1 gram per capillary per minute to about 1.25 grams per capillary per minute, more specifically, from at least about 0.3 gram per capillary per minute to about 1.1 grams per capillary per minute, through a die having a plurality of small diameter extrusion capillaries, as molten threads into a gas stream which attenuates the molten threads to provide a gas-borne stream of microfibers which are then formed into the fibrous nonwoven elastomeric web upon their deposition on a collecting arrangement. The attenuating gas stream is applied to the molten threads at a temperature of from at least about 100 degrees Centigrade to about 400 degrees Centigrade, for example, from about 200 degrees Centigrade to about 350 degrees Centigrade and at a pressure of from at least about 0.5 pound per square inch, gage, to about 20 pounds per square inch, gage, for example, from at least about 1 pound per square inch, gage, to about 10 pounds per square inch, gage. The thread attenuating gas stream may be an inert, non-oxidizing, gas stream such as, for example, a stream of nitrogen gas. In some embodiments the velocity and temperature of the thread-attenuating gas stream is adjusted so that the fibers are collected as substantially continuous fibers having diameters of from about ten (10) microns to about sixty (60) microns, for example, from at least about ten (10) microns to about forty (40) microns. The fibrous nonwoven elastomeric webs so formed will include elastomeric fibers composed of from at least about 10 percent, by weight, of the block copolymer and greater than 0 percent, by weight, and up to about 90 percent, by weight, of the polyolefin. The fibers are usually composed from at least about 20 percent, by weight, to about 95 percent, by weight, of the block copolymer and from at least about 5 percent, by weight, to about 80 percent, by weight of the polyolefin. For example, the fibers may be composed from at least about 30 percent, by weight, to about 90 percent, by weight, of the block copolymer and from at least about 10 percent, by weight, to about 70 percent, by weight, of the polyolefin. Preferably, the fibers are composed from about 50 percent, by weight, to about 90 percent, by weight, of the block copolymer and from at least about 10 percent, by weight, to about 50 percent, by weight, of the polyolefin. For example, the fibers may be composed from at least about 50 percent, by weight, to about 70 percent, by weight, of the block copolymer and from at least about 30 percent, by weight, to about 50 percent, by weight, of the polyolefin.

Another such resiliently stretchable material is disclosed in U.S. patent application, Ser. No. 760,437 in the name of Jack D. Taylor and Michael J. Vander Wielen and assigned to the assignee of the present application, entitled "Composite Elastomeric Material and Process for Making the Same", the disclosure of which is incorporated herein by reference and relied upon. That application provides a method of producing a composite elastic material comprising at least one gatherable web bonded to at least one elastic web, the method comprising (a) tensioning an elastic web (which may comprise a fibrous web such as a nonwoven web of elastomeric fibers, for example, meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The fibrous elastic web can also be maintained in a stretched condition during the bonding, at an elongation of at least about 25 percent, preferably about 25 percent to over 500 percent, for example, about 25 percent to 550 percent elongation during the bonding. The method also includes bonding the elongated elastic web to the gatherable web by overlaying the elastic and gatherable webs and applying heat and pressure to the overlaid webs, for example, by heating bonding sites on the elastic web to a temperature of from at least about 65 degrees Centigrade to about 120 degrees Centigrade, preferably from at least about 70 degrees Centigrade to about 90 degrees Centigrade.

That application also provides an elastic composite material comprising an elastic web bonded to at least one gatherable web which is extensible and contractible with the elastic web upon stretching and relaxing of the composite material, the elastic composite material being made by a method as described above. Also provided is an elastic web that is bonded to the gatherable web at a plurality of spaced-apart locations in a repeating pattern and the gatherable web is gathered between the bonded locations. The elastic web may comprise a nonwoven web of elastomeric fibers, preferably elastomeric microfibers, such as, for example, an elastomeric nonwoven web of meltblown elastomeric fibers or an elastomeric film.

The elastic composite material may include one or more of the following in any combination: the elastomeric fibers, preferably meltblown elastomeric fibers, may be formed from material selected from the group including (i) A-B-A' block copolymers wherein "A" and "A'" may be the same or different endblocks and each is a thermoplastic polymeric endblock or segment which contains a styrenic moiety such as polystyrene or polystyrene homologs, and "B" is an elastomeric polymer midblock or segment, for example, a midblock selected from the group including poly(ethylene-butylene), polyisoprene and polybutadiene, with poly(ethylene-butylene) being preferred and (ii) blends of one or more polyolefins with the A-B-A' block copolymers of (i) where "B" is a poly(ethylene-butylene) midblock; each of the "A" and "A'" endblocks may be selected from the group consisting of polystyrene and polystyrene homologs, for example, poly(alpha methylstyrene), and where the elastomeric fibers are formed from a blend of one or more polyolefins with an A-B-A' block copolymer where "B" is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, for example, the meltblown microfibers, are composed of at least 10 percent, for example at least 20 percent, more specifically at least 30 percent, for example, from about 10 percent to 90 percent, by weight, of the aforesaid A-B-A' block copolymers and greater than 0 percent, by weight, for example, from about 90 percent to about 10 percent, by weight, of the polyolefin; the elastic web, for example, a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter, for example, from about 5 to about 100 grams per square meter, although its basic weight can be much higher; the gatherable web is a nonwoven, non-elastic material, preferably one composed of fibers formed from materials selected from the group including polyester fibers, for example, poly(ethylene terephthalate) fibers, polyolefin fibers, polyamide fibers, for example, nylon fibers, cellulosic fibers, for example, cotton fibers, and mixtures thereof. Alternatively, the gatherable web may be any suitable woven fabric. In a particular aspect, the composition of the A-B-A' polymer used is such that the sum of the molecular weight of "A" with the molecular weight of "A'" is from about 14 to 31 percent (from about 14 to 29 percent when "B" is poly(ethylene-butylene)) of the molecular weight of the A-B-A' block copolymer.

A further such resiliently stretchable material is disclosed in U.S. patent application, Ser. No. 760,449, in the name of Michael J. Morman, and assigned to the assignee of the present invention, entitled "Composite Nonwoven Elastic Web", the disclosure of which is incorporated herein by reference. That application is directed to a process for producing a composite nonwoven elastic web which is composed of a nonwoven elastic web that is joined to a fibrous nonwoven gathered web. In particular, the process disclosed therein produces a composite nonwoven elastic web which, in its relaxed, nonstretched state, is composed of a gathered nonwoven fibrous web that is joined to a nonwoven elastic web with the nonwoven elastic web having been relaxed from a stretched, biased length to a relaxed, unbiased, nonstretched length so as to gather the fibrous nonwoven gathered web. An important feature of the process disclosed therein is that the fibrous nonwoven gatherable web is formed directly onto a surface of the nonwoven elastic web while the nonwoven elastic web is maintained in a stretched, biased and elongated condition. The nonwoven elastic web may be formed by, for example, a meltblowing process or any other process for forming a nonwoven elastic web. For example, the nonwoven elastic web could be an apertured web of an elastic film as opposed to a meltblown fibrous nonwoven elastic web. The formed nonwoven elastic web has a normal relaxed, nonstretched, nonbiased length. Thereafter, the nonwoven elastic web is elongated by being stretched to a stretched, biased length. In a subsequent step of the process a fibrous nonwoven gatherable web may be formed, for example, by either a meltblowing or spinbonding process or any other process for forming a fibrous nonwoven gatherable web, directly upon a surface of the nonwoven elastic web while the nonwoven elastic web is maintained at its elongated, stretched and biased length. During formation of the fibrous nonwoven gatherable web the nonwoven elastic web is maintained at a stretched length which is at least about 125 percent, that is, at least about one and one quarter of the relaxed, unbiased length of the nonwoven elastic web. For example, the stretched, biased length of the nonwoven elastic web may be maintained in the range of from at least about 125 percent of the relaxed, unbiased length of the nonwoven elastic web to about 700 or more percent of the relaxed, unbiased length of the nonwoven elastic web. The fibrous nonwoven gatherable web is joined to the nonwoven elastic web while the nonwoven elastic web is maintained at its elongated stretched, biased length. This results in the formation of a composite nonwoven elastic web which includes the nonwoven elastic web which is joined to the fibrous nonwoven gatherable web. Because the fibrous nonwoven gatherable web is formed directly onto the surface of the nonwoven elastic web while the nonwoven elastic web is being maintained at its stretched, biased length, the nonwoven elastic web is, that this stage in the process, elongated, stretched and biased and the fibrous nonwoven gatherable web is in an ungathered but gatherable condition. In one aspect, the joining of the fibrous nonwoven gatherable web to the nonwoven elastic web is achieved by heat-bonding to fuse the two webs to each other. The heat-bonding may be carried out within the temperature range of from about 50 degrees centigrade below the melt temperature of at least one of the materials utilized to form at least one of the two webs to about the melt temperature of at least one of the materials utilized to form at least one of the two webs. At high through-put rates the heat-bonding can be carried out above the melt temperature of one or more of the materials utilized to form the webs. The heat-bonding may also be carried out under appropriate conventional pressurized conditions. If desired, conventional sonic bonding techniques may be substituted for the heat-bonding steps.

The application also discloses another embodiment whereby the joining of the fibrous nonwoven gatherable web to the stretched nonwoven elastic web is achieved solely by the entanglement of the individual fibers of the fibrous nonwoven gatherable web with the nonwoven elastic web during formation of the fibrous gatherable web on the surface of the elastic web. If the nonwoven elastic web is a fibrous nonwoven elastic web formed by, for example, meltblowing, entanglement of the individual fibers of the fibrous nonwoven gatherable web with the fibrous nonwoven elastic web is achieved by entanglement of the individual fibers of the fibrous gatherable web with the individual fibers of the fibrous elastic web. If the nonwoven elastic web is an apertured film, joining of the fibrous nonwoven web with the film is achieved by entanglement of the individual fibers of the fibrous gatherable web within the apertures of the film. The joining of the two webs to each other can also be achieved by forming the nonwoven elastic web out of a tacky elastic material, a process that will be discussed hereinafter. In addition, the joining of the two webs to each other may be further enhanced by applying pressure to the two webs after the gatherable web has been formed on the surface of the elastic web. Further improvement in the joining of the two webs can be obtained by applying an adhesive material to the upper surface of the nonwoven elastic web prior to formation of the fibrous nonwoven gatherable web thereon.

After joining of the two webs to each other has been achieved to form a composite elastic web, the biasing force is removed from the composite nonwoven elastic web and the composite elastic web is allowed to relax to its normal relaxed, unbiased length. Because the fibrous nonwoven gatherable web is joined to the nonwoven elastic web while the nonwoven elastic web is stretched, relaxation of the composite nonwoven elastic web results in the gatherable web being carried with the contracting nonwoven elastic web and thus being gathered. After gathering of the fibrous nonwoven gatherable web has occurred by reducing the biasing force on the composite nonwoven elastic web, the composite nonwoven elastic web may be rolled up in rolls for storage and shipment of directed to a manufacturing process for the production of products such as the disposable garments taught by the present application.

As indicated above, the process disclosed in U.S. patent application Ser. No. 760,449 can be enhanced by the utilization of a tacky fibrous nonwoven elastic web which can be formed by, for example, meltblowing microfibers of a tacky elastic material such as, for example, an A-B-A' block copolymer or blends of such A-B-A' block copolymers with poly(alpha-methylstyrene) where "A" and "A'" are each thermoplastic polystyrene or polystyrene homolog endblocks and "B" is an elastic polyisoprene midblock. In some embodiments "A" may be the same thermoplastic polystyreme or polystyrene homolog endblock as "A'". The tacky fibrous nonwoven elastic web is then elongated by being stretched to an elongated, stretched length and a fibrous nonwoven gatherable web is formed, for example, by meltblowing or spinbonding the fibrous nonwoven gatherable web, directly upon a surface of the tacky fibrous nonwoven elastic web while maintaining the fibrous nonwoven elastic web at its stretched length. As a result of the fact that the fibrous nonwoven elastic web is tacky, the fibrous nonwoven gatherable web is simultaneously formed upon and adhesively joined to the surface of the tacky fibrous nonwoven elastic web. This results in the formation of a composite nonwoven elastic web having an ungathered fibrous gatherable web adhesively joined to the tacky fibrous nonwoven elastic web with the joining of the two webs to each other being achieved by the adhesive joining which occurs during formation of the fibrous nonwoven gatherable web on the surface of the fibrous nonwoven elastic web. The adhesive joining of the two webs to each other may be increased upon application of pressure to the composite nonwoven elastic web by passing the composite nonwoven elastic web through the nip between rollers, which may be unheated, after the composite web has been formed but before the fibrous tacky nonwoven elastic web is allowed to relax. The adhesive joining may be further enhanced by application of an adhesive material to the surface of the tacky fibrous nonwoven elastic web prior to formation of the gatherable web thereon. The composite nonwoven elastic web is then allowed to relax to its normal relaxed, unbiased length. Because the fibrous nonwoven gatherable web is joined to the tacky fibrous nonwoven elastic web while the tacky fibrous nonwoven elastic web is in a stretched condition, relaxation of the composite nonwoven elastic web and thus the tacky fibrous nonwoven elastic web results in the gatherable web being carried with the contracting fibrous nonwoven elastic web and thus being gathered. After gathering of the fibrous nonwoven gatherable web has occurred the composite nonwoven elastic web may be rolled up in rolls for storage or directly applied to a manufacturing process for the production of disposable garments such as the disposable garments taught by the present application.

The U.S. patent application, Ser. No. 760,449 is also directed to a composite nonwoven elastic web composed of a nonwoven elastic web that is joined to a gatherable fibrous nonwoven web which has been gathered and with the composite web having been formed by any of the embodiments of the process disclosed above. In particular, the composite nonwoven elastic web, in its relaxed, nonstretched state, is composed of a nonwoven elastic web that is joined to a fibrous nonwoven gathered web which has been gathered as a result of the nonwoven elastic web having been relaxed from an elongated stretched, biased length to a relaxed, unbiased nonstretched length. Exemplary elastomeric materials for use in formation of the fibrous nonwoven elastic web include polyester elastomeric materials, polyurethane elastomeric materials, and polyamide elastomeric materials. Other elastomeric materials for use in formation of the fibrous nonwoven elastic web include (a) A-B-A' block copolymers, where "A" and "A'" are each a thermoplastic polymer endblock which includes a styrenic moiety and where "A" may be the same thermoplastic polymer endblock as "A'", such as a poly(vinyl arene), and where "B" is an elastomeric polymer midblock such as a conjugated diene or a lower alkene or (b) blends of one or more polyolefins or poly(alpha-methyl styrene) with A-B-A' block copolymers, where "A" and "A'" are each a thermoplastic polymer endblock which includes a styrenic moiety, where "A" may be the same thermoplastic polymer endblock as "A'", such as a poly(vinyl arene) and where "B" is an elastomeric polymer midblock such as a conjugated diene or a lower alkene. The "A" and "A'" endblocks may be selected from the group including polystyrene and polystyrene homologs and the "B" midblock may be selected from the group including polyisoprene, polybutadiene or poly(ethylene-butylene). If "A" and "A'" are selected from the group including polystyrene or polystyrene homologs and "B" is poly(ethylene-butylene), materials which may be blended with these block copolymers are polymers, including copolymers of ethylene, propylene, butene, other lower alkenes or one or more of these materials. If "A" and "A'" are selected from the group including polystyrene or polystyrene homologs and "B" is a polyisoprene midblock, a material for blending with this type of block copolymer is poly(alpha-methylstyrene).

It is to be clearly understood that the description of methods for making a material suitable for outer cover 20 and the description of materials suitable for use as outer cover 20 is exemplary only and is not meant to be limiting. Other resiliently stretchable materials could be used without departing from the spirit and scope of the present invention.

Various materials are contemplated for use as the absorbent composite including fibrous materials, foams, particulates, etc. In general, the most economical liquid absorbent material for use in disposable diapers has been an absorbent fiber. The absorbent fiber most commonly used in cellulosic fiber such as comminuted wood pulp, commonly known in the art as "pulp fluff", or simply "fluff." Absorbent composites made from these fibers generally have a low density and a high capacity for absorbing fluids, but it has been found that their wicking capability is relatively poor. One prior art approach to solve the relatively poor wicking capability is taught in U.S. Pat. No. 4,213,459, issued to Sigl, assigned to the assignee of the present invention. U.S. Pat. No. 4,213,459 teaches a method wherein the pore sizes of the absorbent composite are decreased such that the improved capillary action of the pores overcomes the force of gravity to cause the waste liquid to move upwardly to other parts of the absorbent composite. Another approach to solve the problem of poor wicking capability is to provide an absorbent composite with at least two layers of cellulosic fibers of different densities or different average pore sizes. The absorbent composite may comprise a first, lower density layer of cellulosic fibers such as fluff which lies directly beneath bodyside liner 42 with a second, higher density layer of fluff beneath the first layer. Predominantly softwood pulp fluff could be used for each of the above-described layers. Alternatively, a layer of predominantly softwood fluff can be used for the first layer and a layer of preponderantly hardwood fluff could be used for the second layer, in which case it is the average pore size and not necessarily the density that varies between the first and second layers. For the purposes of this disclosure, "predominantly" is intended to mean at least about 80% while "preponderantly" is intended to mean at least about 50%. Another alternative is to vary the pore size without necessarily varying the density. This can be done because hardwood fluff has a smaller pore size than softwood fluff and as a result, if hardwood fluff fibers are used as a replacement for the higher density softwood fluff fibers, two different pore size distributions will be obtained, even if the density of each layer is the same. Thus, for example, a two component fluff sandwich comprising a coarse pore structure in the first layer obtained from a predominantly softwood fluff pulp and a fine pore structure in the second layer comprised of a preponderantly hardwood fluff, densified throughout to one density can be used.

A second aspect relating to the absorbent composite relates to including a portion of a hydrogel as part of the absorbent composite. The term "hydrogel" as used herein refers to one or more hydrocolloid materials capable of absorbing many times their own weight of water or aqueous fluid. These materials ae generally prepared by polymerizing one or more monomers which, if homopolymerized by conventional methods, would form water soluble polymers. To render them water-insoluble and suitable for the present invention, these polymers or mixture of polymers are typically reacted, frequently with a crosslinking agent, to form crosslinked polymers, thereby introducing a limited water-insolubility while retaining susceptibility to swelling in water and water-containing fluids. Pseudo-crosslinking may also be achieved by chain entanglement of high-molecular weight polymers, thus effecting water insolubility. Typically, these hydrocolloids are salts of polyacrylic acid and variations thereof, such as methacrylic acid. Commercially they are available under such trademarks WATER LOCK from Grain Processing Company; ARASORB 720 from Arakawa Chemical, Inc. (U.S.A.); and AQUALIC-CA from Nippon Shakubai/Japanese Catalytic Chemical Co. Alternative hydrogels may also include hydrophilic polymers grafted onto starch or cellulose backbones and crosslinked carboxylated celluloses.

The hydrogel may be sandwiched between a first higher density layer and a second higher density layer or between a low density layer and a high density layer. The hydrogel may be also disposed adjacent to a higher density layer which is in turn covered with a lower density layer. In addition to the absorbent composite being structured in layers, the hydrogel material may be disposed within the absorbent composite as a powder, fiber, etc., forming a mixture. The absorbent composite, in that case, may be provided with uniform densification of all layers to about 0.1 g/cc., or in the range of about 0.1 g/cc. to about 0.35 g/cc.

The term "density" as used herein refers to the density of the composite structure of the lower density layer or the higher density layer, and not the actual fiber density. (The actual fiber density is about 1.5 g/cc.) The density of the lower density layer should be in the range of about 0.03 to about 0.14 g/cc., with the preferred range at about 0.07 to about 0.11 g/cc. The higher density layer should have a density in the range of about 0.14 to about 0.35 g/cc., and preferably in the range of about 0.16 to about 0.3 g/cc. for providing the desired capillarity without excessive stiffness. The density for these preferred ranges is a density measured under a load of 0.2 psi.

Comminuted wood pulp (fluff) is preferred as an absorbent fiber, but other cellulose fibers such as cotton linters can be used. The preferred fluff is southern pine kraft wood pulp (i.e., made according to the sulfate process commonly known in the art) which has been bleached, such as can be purchased from International Paper Company. A suitable hardwood fluff pulp is Southern Hardwood Kraft obtainable from Weyerhaueser Company as "New Bern 309."

Alternate embodiments may be utilized without departing from the spirit of the invention. For example, the densified fluff layer could also be used with other absorbents such as coformed (meltblown polymer fibers combined with wood pulp and/or stable fibers) webs, carded webs, air-formed (staple wood pulp blends) webs, and the like, at a lower density.

According to a further aspect of the present invention, the absorbent composite may comprise a mixture of a hydrogel material with 2-98% by weight of a filler material. The "filler materials" may include a wide variety of materials in powder, fiber, or particulate form such as an absorbent fiber wherein the absorbent fiber may be a cellulosic fiber (as described above), a hydrophilic material or a hydrophobic material. The filler materials may be treated with a surfactant to improve surface wetability. Examples include polyolefins such as polyethylene, polypropylene, and polystyrene, as well as natural, slightly absorbent clays, micas or vegetable (for example, corn cob) debris, as well as blends of these materials. See U.S. Pat. No. 4,381,782 to Mazurak et al., the disclosure of which is incorporated herein by reference and relied upon.

Surfactants which may be utilized in accordance with the invention include ionic and nonionic materials such as AEROSOL O. T. (American Cyanamid), TEEPOL 610 (Particle Data Laboratories, Ltd.), NEODOL-27 (Shell Chemical Company), DUOMEEN-361 (Armour Industrial Chemical Company) and TRITON X-102 (Rohm and Haas Co.).

The filler material is first uniformly wetted with up to about 20% by weight of surfactant solution containing surfactant in the range of from about 0.5% to 2.5% by weight. The hydrogel powder is then added and the admixture thoroughly blended to provide an intimate mixture and integration throughout of the components. The hydrogel particles will swell slightly and adhere to the filler material. After drying, the admixture is preferably subjected to slight mechanical action destroying lumps. In use the filler material acts to rapidly wick liquid throughout the mixture and substantially eliminate the tendency to form gel blocks. While it is not desired to limit the invention to any particular theory, it is believed that the surfactant liquid slightly swells the dry hydrogel making it sticky and allowing it to adhere to filler particles. For this reason it is preferred that the filler be damp, including up to 10% by weight of water prior to mixing with surfactant solution.

The amounts of filler material are in the range of 2-98% by weight with the preferred amount being in the range of 5% to 95% and, even more preferably, 25% to 75%, based on the weight of hydrogel material.

The surfactant is preferably added to filler material in an amount of about 0.05% to 0.5% and, more preferably, 0.1% to 0.2% by weight based on the amount of nonabsorbent filler. The filler material is of relatively large average particle diameter in the range of from 1-10,000, preferably 1-1,000, and, most preferred 10-100 times the average hydrogel particle diameter.

Thus, while the invention has now been described with reference to several preferred embodiments and illustrated with regard to a range of optional features, those skilled in the art will appreciate that various substitutions, omissions, modifications, and changes may be made without departing from the spirit hereof. Accordingly, it is intended that the foregoing description be deemed merely exemplary of the preferred scope of the present invention and not to be deemed a limitation thereof.

I claim:

1. An anatomically form-fitting, generally self-adjusting disposable absorbent garment comprising:
   a breathable elastomeric nonwoven outer cover resiliently stretchable in at least one direction wherein said at least one direction is at a selected angle measured from a cross-body direction, said cover comprising a nonwoven elastic web joined to one or more gatherable nonwoven webs, including a waist opening, a pair of leg openings, a central crotch section between said leg openings and front and rear panels separated by said crotch section;
   an absorbent insert structure substantially superposable on said front and rear panels and said crotch section, including a liquid permeable bodyside liner and a liquid impermeable barrier with an absorbent core disposed therebetween; and
   attachment means for attaching and integrating said insert to said outer cover while allowing substantially unrestricted functional stretchability thereof.

2. The disposable garment of claim 1 further comprising fastening means for securing said disposable garment around a wearer.

3. The invention of claim 2 further comprising full-length releasably engageable fastening means for effecting a substantially full-length, continuous and noncollapsible closure from said waist opening to each of said leg openings thereby maintaining the dimensional integrity of said garment.

4. The invention of claim 3 further comprising fixed position fastening means, fastenable only at fixed positions on said outer cover, for providing discrete target locations assuring proper fastening of said garment on a wearer.

5. The invention of claim 1 wherein said elastic nonwoven web of said outer cover comprises an extruded elastomeric nonwoven material joined to said one or more gatherable webs while said elastomeric web is stretched in at least one direction.

6. The invention of claim 5 wherein said extruded elastomeric material comprises a meltblown polymeric material and said one or more gatherable nonwoven webs comprise either spunbonded, meltblown, carded, costructured or other nonwoven webs.

7. The invention of claim 6 wherein said meltblown polymeric material of said elastic web comprises a polyolefin blended and meltblown with one or more elastomeric polymer materials.

8. The invention of claim 7 wherein said elastomeric polymer material of said elastic web comprises an A-B-A block copolymer.

9. The invention of claim 8 wherein said A-B-A block copolymer comprises an A-B-A' block copolymer.

10. The garment of claim 1 wherein said outer cover is also liquid permeable.

11. The invention of claim 1 wherein either of said leg and waist openings have a tensioned elastic member extending therealong for further gathering an associated one of said openings about a wearer.

12. The invention of claim 11 wherein said tensioned elastic members complement said resiliently stretchable outer cover to further gather said garment about the body of a wearer.

13. The invention of claim 1 wherein said outer cover comprises a stretch-bonded nonwoven laminate wherein said elastic nonwoven web is bonded to said one or more gatherable nonwoven webs while said elastic nonwoven web is in a stretched condition.

14. The invention of claim 1 wherein said absorbent insert structure is attached and integrated into said outer cover while said outer cover is in a stretched condition.

15. The invention of claim 14 wherein said outer cover is stretched in a direction essentially cross body to the wearer prior to said insert being integrated thereinto.

16. The invention of claim 15 wherein said attachment means comprise autogenous bonds bonding said insert to said outer cover.

17. The invention of claim 16 wherein said autogenous bonds are generated thermally or ultrasonically.

* * * * *

UNITED STATES PATENT AND TRADEMARK OFFICE
CERTIFICATE OF CORRECTION

PATENT NO. : 4,701,174
DATED : October 20, 1987
INVENTOR(S) : Lynn A. Johnson

It is certified that error appears in the above-identified patent and that said Letters Patent is hereby corrected as shown below:

Column 8, Line 15, delete "over" and substitute therefor -- other --.

Column 11, Line 36, delete "20" and substitute therefor -- 90 --.

Column 12, Line 58, delete "stape" and substitute therefor -- staple --.

Column 12, Line 62, delete "1 1/2" and substitute therefor -- 1 7/8 --.

Column 12, Line 64, delete "is" and substitute therefor -- it --.

Column 12, Line 68, delete "spuns" and substitute therefor -- spun --.

Column 13, Line 59, delete "0".

Column 14, Line 49, delete "and" and substitute therefor -- of --.

Column 18, Line 2, delete "basic" and substitute therefor -- basis --.

Column 19, Line 6, delete "that" and substitute therefor -- at --.

UNITED STATES PATENT AND TRADEMARK OFFICE
CERTIFICATE OF CORRECTION

PATENT NO. : 4,701,174

DATED : October 20, 1987

INVENTOR(S) : Lynn A. Johnson

It is certified that error appears in the above-identified patent and that said Letters Patent is hereby corrected as shown below:

Column 22, line 29, delete "ae" and substitute therefor -- are --.

Signed and Sealed this

Second Day of January, 1990

Attest:

JEFFREY M. SAMUELS

Attesting Officer     Acting Commissioner of Patents and Trademarks